(12) United States Patent
Clark et al.

(10) Patent No.: US 12,076,078 B2
(45) Date of Patent: *Sep. 3, 2024

(54) IRRIGATED ABLATION CATHETER HAVING IRRIGATION PORTS WITH REDUCED HYDRAULIC RESISTANCE

(71) Applicant: Biosense Webster (Israel) Ltd., Yokneam (IL)

(72) Inventors: Jeffrey L. Clark, Castaic, CA (US); Jeffry Tola, Los Angeles, CA (US)

(73) Assignee: BIOSENSE WEBSTER (ISRAEL) LTD. (IL)

( * ) Notice: Subject to any disclaimer, the term of this patent is extended or adjusted under 35 U.S.C. 154(b) by 21 days.

This patent is subject to a terminal disclaimer.

(21) Appl. No.: 17/141,112

(22) Filed: Jan. 4, 2021

(65) Prior Publication Data

US 2021/0145512 A1 May 20, 2021

Related U.S. Application Data

(63) Continuation of application No. 15/919,131, filed on Mar. 12, 2018, now Pat. No. 10,881,457, which is a
(Continued)

(51) Int. Cl.
*A61B 18/14* (2006.01)
*A61M 25/01* (2006.01)
(Continued)

(52) U.S. Cl.
CPC .......... *A61B 18/1492* (2013.01); *A61B 18/14* (2013.01); *A61M 25/0127* (2013.01);
(Continued)

(58) Field of Classification Search
CPC ................ A61B 18/14; A61B 18/1492; A61B 2018/147; A61B 2018/00029;
(Continued)

(56) References Cited

U.S. PATENT DOCUMENTS

| | | |
|---|---|---|
| 4,770,171 A | 9/1988 | Sweren et al. |
| 5,391,199 A | 2/1995 | Ben-Haim |

(Continued)

FOREIGN PATENT DOCUMENTS

| | | |
|---|---|---|
| CN | 101332083 A | 12/2008 |
| CN | 101528145 A | 9/2009 |

(Continued)

OTHER PUBLICATIONS

Partial European Search Report dated Oct. 8, 2009, for European Patent Application No. 09251788.7, 8 pages.
(Continued)

*Primary Examiner* — Thomas A Giuliani
(74) *Attorney, Agent, or Firm* — Frost Brown Todd LLP

(57) ABSTRACT

An irrigated ablation catheter includes a tip electrode with a thin shell and a plug to provide a plenum chamber. The tip electrode has an inlet of a predetermined size and noncircular shape, and outlets in the form of fluid ports formed in the thin shell wall. The plurality of the fluid ports is predetermined, as is their diameter. Each fluid port has a tapered configuration, for example, a frustoconical configuration, with a smaller inlet diameter and a larger outlet diameter.

20 Claims, 22 Drawing Sheets

Related U.S. Application Data continuation of application No. 15/369,792, filed on Dec. 5, 2016, now Pat. No. 9,913,685, which is a continuation of application No. 13/789,574, filed on Mar. 7, 2013, now Pat. No. 9,510,894, which is a continuation-in-part of application No. 12/770,582, filed on Apr. 29, 2010, now Pat. No. 9,943,363, and a continuation-in-part of application No. 12/769,592, filed on Apr. 28, 2010, now Pat. No. 9,943,362, said application No. 12/770,582 is a continuation of application No. 12/769,592, filed on Apr. 28, 2010, now Pat. No. 9,943,362.

(51) Int. Cl.
  *A61B 18/00* (2006.01)
  *A61B 34/20* (2016.01)
  *A61M 25/00* (2006.01)

(52) U.S. Cl.
  CPC ........... *A61B 2018/00029* (2013.01); *A61B 2018/00357* (2013.01); *A61B 2018/00577* (2013.01); *A61B 2034/2051* (2016.02); *A61B 2218/002* (2013.01); *A61M 2025/0073* (2013.01)

(58) Field of Classification Search
  CPC  A61B 2018/00357; A61B 2018/00577; A61B 2018/00005; A61B 2018/00011; A61B 2018/00065; A61B 2018/1465; A61B 2018/1472; A61B 2218/002; A61M 2025/0073
  USPC ...... 606/41, 42, 46, 47, 49; 607/98, 99, 101, 607/104, 105, 113, 115, 116
  See application file for complete search history.

(56) References Cited

U.S. PATENT DOCUMENTS

| | | | |
|---|---|---|---|
| 5,419,767 A | 5/1995 | Eggers et al. | |
| 5,462,521 A | 10/1995 | Brucker et al. | |
| 5,545,161 A | 8/1996 | Imran | |
| 5,582,609 A | 12/1996 | Swanson et al. | |
| 5,688,267 A | 11/1997 | Panescu et al. | |
| 5,735,846 A | 4/1998 | Panescu et al. | |
| 5,800,428 A | 9/1998 | Nelson et al. | |
| 5,800,432 A | 9/1998 | Swanson | |
| 5,904,651 A | 5/1999 | Swanson et al. | |
| 5,947,988 A | 9/1999 | Smith | |
| 5,964,757 A | 10/1999 | Ponzi | |
| 6,110,196 A | 8/2000 | Edwards | |
| 6,129,698 A | 10/2000 | Beck | |
| 6,210,411 B1 | 4/2001 | Hofmann et al. | |
| 6,217,576 B1 | 4/2001 | Tu et al. | |
| 6,458,123 B1 | 10/2002 | Brucker et al. | |
| 6,464,694 B1 | 10/2002 | Massengill | |
| 6,576,858 B1 | 6/2003 | Yokomichi | |
| 6,690,963 B2 | 2/2004 | Ben-Haim et al. | |
| 7,104,989 B2 | 9/2006 | Skarda | |
| 7,258,689 B2 | 8/2007 | Salvo | |
| 7,549,989 B2 | 6/2009 | Morgan et al. | |
| 7,815,635 B2 | 10/2010 | Wittkampf et al. | |
| 7,901,403 B2 | 3/2011 | Woloszko et al. | |
| 8,224,422 B2 | 7/2012 | Mottola et al. | |
| 8,348,888 B2 | 1/2013 | Selkee | |
| 8,500,730 B2 | 8/2013 | Lee et al. | |
| 8,945,117 B2* | 2/2015 | Bencini | A61B 18/1492 606/41 |
| 9,510,894 B2* | 12/2016 | Clark | A61B 18/1492 |
| 9,913,685 B2* | 3/2018 | Clark | A61B 18/1492 |
| 9,943,362 B2 | 4/2018 | Clark et al. | |
| 9,943,363 B2 | 4/2018 | Clark et al. | |
| 10,881,457 B2* | 1/2021 | Clark | A61B 18/14 |
| 2001/0025179 A1 | 9/2001 | Levine | |
| 2001/0051802 A1 | 12/2001 | Woloszko et al. | |
| 2003/0009094 A1* | 1/2003 | Segner | A61B 5/062 600/374 |
| 2003/0163178 A1 | 8/2003 | Davison et al. | |
| 2003/0212394 A1 | 11/2003 | Pearson et al. | |
| 2004/0243157 A1 | 12/2004 | Connor et al. | |
| 2005/0085769 A1 | 4/2005 | MacMahon et al. | |
| 2006/0184165 A1 | 8/2006 | Webster, Jr. et al. | |
| 2006/0241577 A1 | 10/2006 | Balbierz et al. | |
| 2006/0264808 A1 | 11/2006 | Staid et al. | |
| 2007/0156114 A1 | 7/2007 | Worley et al. | |
| 2007/0156132 A1 | 7/2007 | Drysen | |
| 2007/0270791 A1 | 11/2007 | Wang et al. | |
| 2007/0287998 A1 | 12/2007 | Sharareh et al. | |
| 2008/0161792 A1* | 7/2008 | Wang | A61B 18/1492 606/41 |
| 2008/0255540 A1 | 10/2008 | Selkee | |
| 2008/0287944 A1 | 11/2008 | Pearson et al. | |
| 2009/0093810 A1* | 4/2009 | Subramaniam | A61N 1/06 606/41 |
| 2009/0093811 A1 | 4/2009 | Koblish et al. | |
| 2009/0125016 A1 | 5/2009 | Wang et al. | |
| 2009/0209949 A1 | 8/2009 | Ingle et al. | |
| 2010/0030209 A1 | 2/2010 | Govari et al. | |
| 2010/0069834 A1 | 3/2010 | Schultz | |
| 2010/0168827 A1 | 7/2010 | Schultz | |
| 2011/0009857 A1 | 1/2011 | Subramaniam et al. | |
| 2011/0264089 A1 | 10/2011 | Zirkle et al. | |
| 2011/0270244 A1* | 11/2011 | Clark | A61B 18/1492 606/41 |
| 2011/0270246 A1* | 11/2011 | Clark | A61B 18/1492 606/41 |
| 2018/0228541 A1 | 8/2018 | Clark et al. | |

FOREIGN PATENT DOCUMENTS

| | | |
|---|---|---|
| CN | 101617957 A | 1/2010 |
| CN | 102232870 A | 11/2011 |
| EP | 0 956 826 A2 | 11/1999 |
| EP | 0 982 047 A2 | 3/2000 |
| EP | 1 690 510 A1 | 8/2006 |
| EP | 1 803 410 A1 | 7/2007 |
| EP | 2 145 596 A1 | 1/2010 |
| EP | 2 380 519 A1 | 10/2011 |
| EP | 2 382 935 A1 | 11/2011 |
| JP | H 06-254103 | 9/1994 |
| JP | H 11-504539 | 4/1999 |
| JP | 2006-239414 A | 9/2006 |
| JP | 2009-148550 A | 7/2009 |
| JP | 2010-505592 A | 2/2010 |
| JP | 2011-229920 A | 11/2011 |
| WO | WO 02/083228 A3 | 10/2002 |
| WO | WO 2011/008681 A1 | 1/2011 |

OTHER PUBLICATIONS

European Patent Office Search Report dated Aug. 4, 2011, for European Patent Application No. 11163515.7, 6 pages.
European Search Report dated Feb. 2, 2012 from EP Patent Application No. EP 12151275, 2 pages.
Extended European Search Report for corresponding Application No. EP 11163898.7-1269, dated Jul. 29, 2011, 6 pages.
Extended European Search Report for EP Application No. 14158294.0-1652, dated May 26, 2014, 7 pages.
English translation of JP Office Action dated Nov. 11, 2014 for Japanese Patent Application No. 2011-096838, 3 pgs.
State Intellectual Property Office of People's Republic China Search Report for Application No. 200910159385.5, dated Jul. 30, 2012, English language translation only, 2 pages.
English translation of CN Search Report dated May 23, 2014, issued in corresponding CN Application No. 201110118159, 3 pages.
European Examination Report dated Jul. 10, 2017, issued in corresponding EP Application No. 11163515.7, 5 pages.
English Translation of Japanese Office Action dated Dec. 19, 2017 for Japanese Patent Application No. 2014-043592, 4 pages.

(56) References Cited

OTHER PUBLICATIONS

English Translation of Japanese Office Action dated Jul. 5, 2016 for Japanese Patent Application No. 2011-99075, 4 pages.
English Translation of Japanese Office Action dated Nov. 11, 2014 for Japanese Patent Application No. 2011-099075, 4 pages.
Extended European Search Report dated Feb. 9, 2012 for Application No. EP 12151275, 6 pages.
English Translation of Chinese Second Office Action dated Feb. 14, 2018 for Chinese Patent Application No. 201410081748.9, 3 pages.
English Translation of Chinese First Office Action dated Jun. 6, 2017 for Chinese Patent Application No. 201410081748.9, 4 pages.
English Translation of Chinese Search Report dated May 25, 2017 for Chinese Patent Application No. 201410081748.9, 3 pages.
Canadian Office Action dated Feb. 8, 2018 for Canadian Patent Application No. 2,738,000, 4 pages.
Canadian Office Action dated May 5, 2017 for Canadian Patent Application No. 2,738,000, 4 pages.
Australian Examination Report No. 1 dated Oct. 9, 2017 for Australian Patent Application No. 2014200882, 4 pages.
Australian Examination Report No. 2 dated Jun. 29, 2015 for Australian Patent Application No. 2011201883, 3 pages.
Australian Examination Report No. 1 dated May 29, 2014 for Australian Patent Application No. 2011201883, 3 pages.
Australian Examination Report No. 1 dated Aug. 19, 2016 for Australian Patent Application No. 2016201304, 4 pages.
Australian Examination Report No. 1 dated Aug. 9, 2016 for Australian Patent Application No. 2015203554, 3 pages.
English Translation of Chinese Second Office Action for Chinese Patent Application No. 201110118159, dated Jan. 12, 2015, 2 pages.
English Translation of Chinese First Office Action for Chinese Patent Application No. 201110118159, dated Jun. 4, 2014, 9 pages.
English Translation of Text of Chinese First Office Action for CN Patent Application No. 201410081748.9, dated Jun. 6, 2017, 2 pages.

* cited by examiner

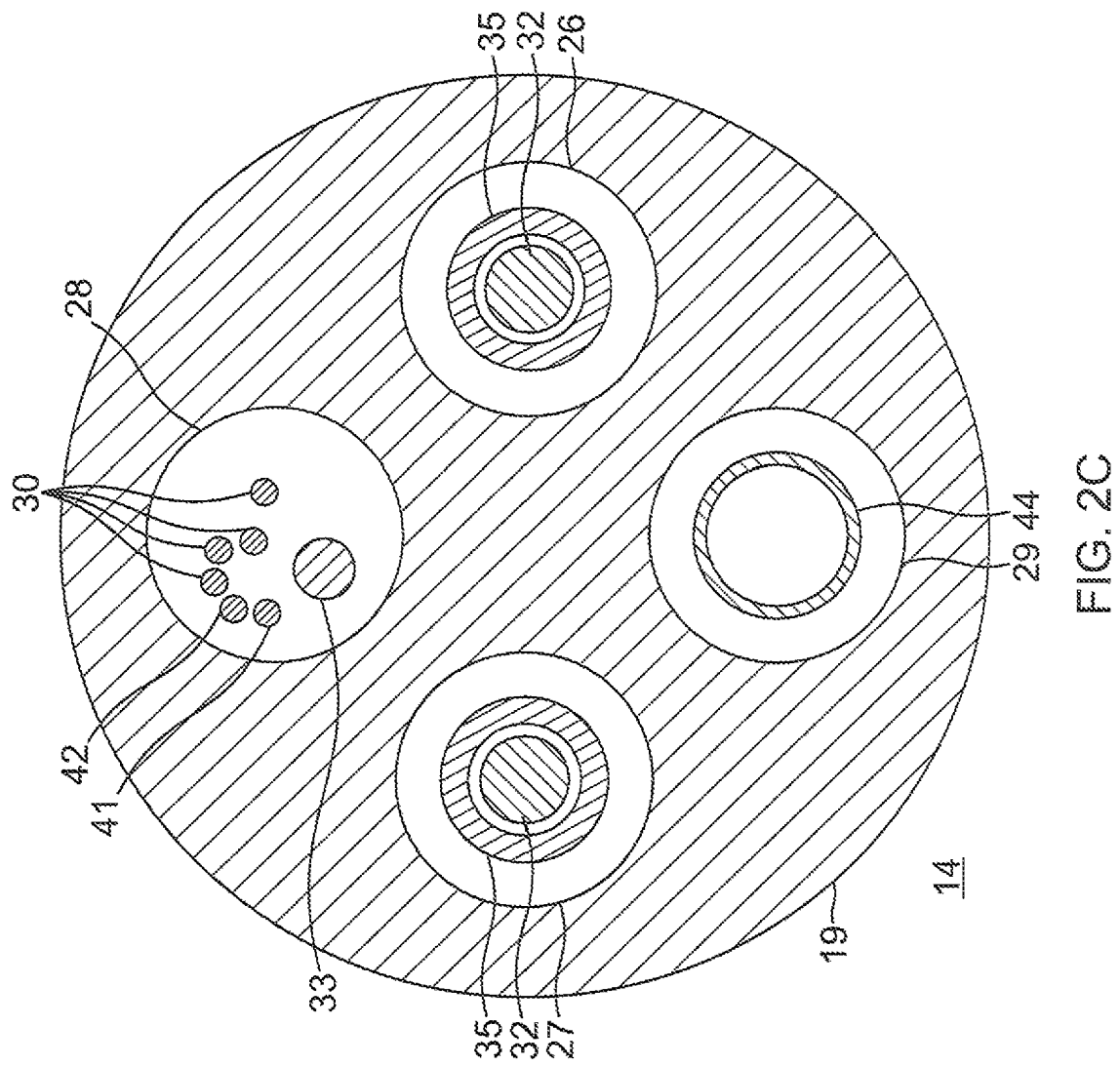

CFD of Irrigation Port Pressure Drop Sensitivity at 15 ml/min

Response Surface Regression: Axial Pressure versus Flow, Hole Size, Taper Angle

The analysis was done using coded units.
Estimated Regression Coefficients for Axial Pressure Drop

| Term | Coef | SB Coef | T | P |
|---|---|---|---|---|
| Constant | 0.123860 | 0.02667 | 4.645 | 0.000 |
| Flow | 0.080077 | 0.03227 | 2.481 | 0.025 |
| Hole Size | -0.151524 | 0.03227 | -4.695 | 0.000 |
| Taper Angle | -0.002541 | 0.03227 | -0.079 | 0.938 |

$S = 0.119261$    PRESS = 0.397994
$R\text{-}Sq = 63.81\%$    $R\text{-}Sq(pred) = 36.70\%$    $R\text{-}Sq(adj) = 57.02\%$ Estimated Regression Coefficients for Axial Pressure Drop using data in uncoded units

| Term | Coef |
|---|---|
| Constant | 0.456436 |
| Flow | 0.0103996 |
| Hole Size | -126.270 |
| Taper Angle | -7.11711E-04 |

Regression Table for Irrigation Port Pressure Drop Model

FIG. 16

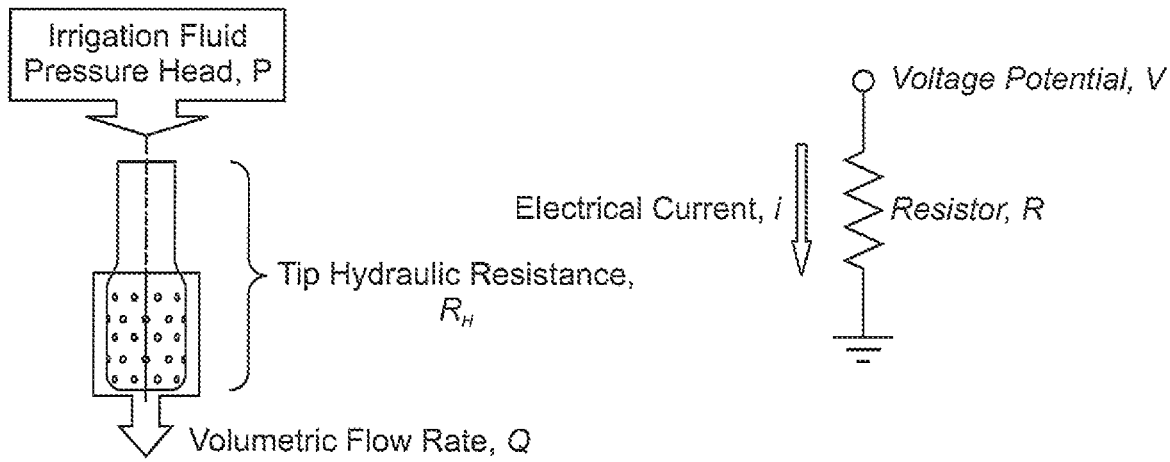

Irrigated Tip Shell Hydraulic and Electrical Analogs

FIG. 17

Hydraulic Resistance Characterization Fixture

| Tip Configuration Name | JM Lot # | Number of ports | Mean Port Diameter Top / Bottom[in] | Total Port Area [in²] | Mean Port Taper Angle [deg] |
|---|---|---|---|---|---|
| LR-TR-0012172 | 645719 | 56 | 0.00279 / - | 3.416×10⁻⁴ | 0 |
| MR-TR-0012172 | 645866 | 56 | 0.00497 / - | 10.877×10⁻⁴ | 0 |
| EDM Nominal - Production | 201103090188 | 56 | .00345 / - | 5.223×10⁻⁴ | 0 |
| Laser-Hi | 201105190120 / 687577 | 56 | 0.00402 / 0.00335 | 4.949×10⁻⁴ | 0 |

| Tip Configuration Name | JM Lot # | Number of ports | Mean Port Diameter Top / Bottom [in] | Total Port Area [in²] | Mean Port Taper Angle [deg] | 8ml/min Port Resistance $R_{H_n}$ $\frac{psi\ min}{ml}$ | 15ml/min Port Resistance $R_{H_n}$ $\frac{psi\ min}{ml}$ |
|---|---|---|---|---|---|---|---|
| LR-TR-0012172 | 645719 | 56 | 0.00279 / - | 3.416 x10⁻⁴ | 0 | 3.31 | 2.55 |
| MR-TR-0012172 | 645866 | 56 | 0.00497 / - | 10.877 x10⁻⁴ | 0 | 1.00 | .70 |
| EDM Nominal - Production | 201103090188 | 56 | .00345 / - | 5.223 x10⁻⁴ | 0 | 1.61 | 1.27 |
| Laser-Hi | 201105190120 / 687577 | 56 | 0.00402 / 0.00335 | 4.949 x10⁻⁴ | 6 | 1.69 | 1.30 |

Laser versus EDM Nom Production Correlation

FIG. 22

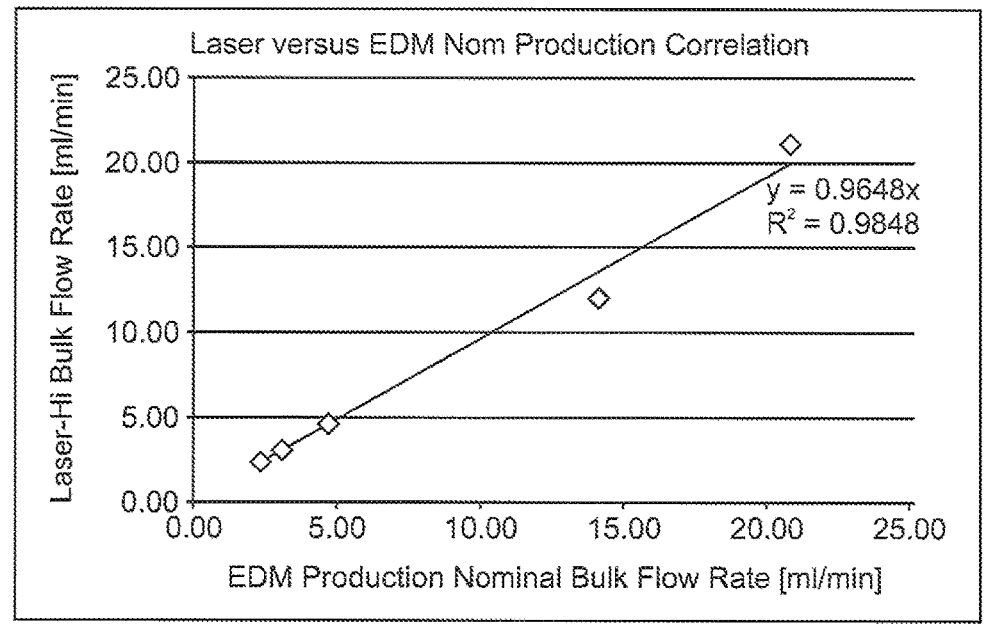

Correlation of Laser and EDM Tips

FIG. 23

Correlation of Laser and EDM Tips using area normalized flow rates

| Flow Rate [ml/min] | Port Bottom Diameter [in] | Individual Port Hydraulic Resistance, $R_{H_n}$ $\frac{psi\ min}{ml}$ |
|---|---|---|
| 8 | 0.005 - 0.003 | 1.00 - 3.31 |
| 15 | 0.005 - 0.003 | 0.70 - 2.55 |

| Tip Type | Flow Rate [ml/min] | Port Bottom Diameter [in] | Individual Port Hydraulic Resistance, $R_{H_n}$ $\frac{psi\ min}{ml}$ |
|---|---|---|---|
| Validation, EDM | 8 | 0.005 - 0.003 / 0° | 1.00 - 3.31 |
|  | 15 | 0.005 - 0.003 / 0° | 0.70 - 2.55 |
| Production, EDM | 8 | 0.004 - 0.003 / 0° | 1.50 - 3.31 |
|  | 15 | 0.004 - 0.003 / 0° | 1.11 - 2.55 |
| Production, Laser | 8 | 0.004 - 0.003 / 6° | 1.47 - 3.24 |
|  | 15 | 0.004 - 0.003 / 6° | 1.09 - 2.50 |

Hydraulic resistance of laser drilled ports relative to validated specification limits

IRRIGATED ABLATION CATHETER HAVING IRRIGATION PORTS WITH REDUCED HYDRAULIC RESISTANCE

RELATED APPLICATIONS

This application is a continuation of and claims priority to and the benefit of patent application Ser. No. 15/919,131 filed Mar. 12, 2018, now U.S. Pat. No. 10,881,457, which is a continuation of and claims priority to and the benefit of patent application Ser. No. 15/369,792 filed Dec. 5, 2016, now U.S. Pat. No. 9,913,685, which is a continuation of and claims priority to and the benefit of application Ser. No. 13/789,574 filed Mar. 7, 2013, now U.S. Pat. No. 9,510,894, which is a continuation-in-part of and claims priority to and the benefit of application Ser. No. 12/769,592, filed Apr. 28, 2010 now U.S. Pat. No. 9,943,362, and application Ser. No. 12/770,582, filed Apr. 29, 2010 now U.S. Pat. No. 9,943,363, which application Ser. No. 12/770,582 is a continuation of and claims priority to and the benefit of application Ser. No. 12/769,592, the entire contents of all of which are incorporated herein by reference.

FIELD OF INVENTION

The present invention relates to an electrophysiologic catheter that is particularly useful for ablation and sensing electrical activity of heart tissue.

BACKGROUND OF INVENTION

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reentrant type, cardiac arrhythmias may also have a focal origin, such as when an isolated region of tissue in an atrium fires autonomously in a rapid, repetitive fashion. Ventricular tachycardia (V-tach or VT) is a tachycardia, or fast heart rhythm that originates in one of the ventricles of the heart. This is a potentially life-threatening arrhythmia because it may lead to ventricular fibrillation and sudden death.

Diagnosis and treatment of cardiac arrythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure—mapping followed by ablation—electrical activity at points within the heart is typically sensed and measured by advancing a catheter containing one or more electrical sensors (or electrodes) into the heart, and acquiring data at a multiplicity of points. These data are then utilized to select the endocardial target areas at which ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a tip electrode at its distal end into a heart chamber. A reference electrode is provided, generally taped to the skin of the patient or by means of a second catheter that is positioned in or near the heart. RF (radio frequency) current is applied to the tip electrode of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60.degree. C., a thin transparent coating of dehydrated blood protein can form on the surface of the electrode. If the temperature continues to rise, this dehydrated layer can become progressively thicker resulting in blood coagulation on the electrode surface. Because dehydrated biological material has a higher electrical resistance than endocardial tissue, impedance to the flow of electrical energy into the tissue also increases. If the impedance increases sufficiently, an impedance rise occurs and the catheter must be removed from the body and the tip electrode cleaned.

In a typical application of RF current to the endocardium, circulating blood provides some cooling of the ablation electrode. However, there is typically a stagnant area between the electrode and tissue which is susceptible to the formation of dehydrated proteins and coagulum. As power and/or ablation time increases, the likelihood of an impedance rise also increases. As a result of this process, there has been a natural upper bound on the amount of energy which can be delivered to cardiac tissue and therefore the size of RF lesions. Historically, RF lesions have been hemispherical in shape with maximum lesion dimensions of approximately 6 mm in diameter and 3 to 5 mm in depth.

It is desirable to reduce or eliminate impedance rises and, for certain cardiac arrhythmias, to create larger lesions. One method for accomplishing this is to irrigate the ablation electrode, e.g., with physiologic saline at room temperature, to actively cool the ablation electrode instead of relying on the more passive physiological cooling of the blood. Because the strength of the RF current is no longer limited by the interface temperature, current can be increased. This results in lesions which tend to be larger and more spherical, usually measuring about 10 to 12 mm.

The effectiveness of irrigating the ablation electrode is dependent upon the distribution of flow within the electrode structure and the rate of irrigation flow through the tip. Effectiveness is achieved by reducing the overall electrode temperature and eliminating hot spots in the ablation electrode which can initiate coagulum formation.

More channels and higher flows are more effective in reducing overall temperature and temperature variations, i.e., hot spots. However, the coolant flow rate should be balanced against the amount of fluid that can be injected into a patient and the increased clinical load required to monitor and possibly refill the injection devices during a procedure. In addition to irrigation flow during ablation, a maintenance flow, typically at a lower flow rate, is required throughout the procedure to prevent backflow of blood flow into the coolant passages. Thus reducing coolant flow by utilizing it as efficiently as possible is a desirable design objective.

The arrangement of conventional internal catheter components such as irrigation lumens, location sensor and related electrical leads is limited by available cross-sectional area of the tip electrode. The limiting direction is typically in the radial direction emanating from the axial centerline of the tip electrode radiating to the outer periphery. Conventional irrigation tubings or the through-passage formed in the tip electrode receiving an irrigation tubing has a circular cross-section and is therefore limited in size by this radial dimension. Furthermore it is generally desirable to have the largest possible fluid lumen in order to minimize hydraulic resistance/pressure drop over the length of the catheter shaft. These factors can often result in a design using either a smaller-than-desired fluid lumen, or a two-piece tubing possessing a larger diameter in the catheter shaft and a smaller diameter coupler at the tip electrode. The inclusion of the coupler results in an additional adhesive bond joint which contributes to a higher risk of fluid leaks.

Moreover, conventional irrigated ablation tip electrodes are designed as solid monolithic structures with internal fluid paths and fluid ports where the internal fluid paths are much longer, if not two, three, or four times longer, than the size of the fluid port. Where fluid flow along the length of the catheter shaft is assumed to be laminar, Poiseuille's law states that pressure drop over a distance is proportional to the flow rate multiplied by the hydraulic resistance, where hydraulic resistant relates fluid viscosity and conduit geometry. Because of the temperature of the irrigating fluid and consequently the high viscosity of the fluid relative to the port diameter, and the length of the irrigation tubing, a significant amount of energy is required to pump the fluid to the tip electrode.

Conventional irrigated ablation tip electrodes also typically have a much greater total fluid output area compared to fluid input area where the fluid output area is a two, three or four multiple of the fluid input area. As such, the flow of irrigation fluid out of the outlet fluid ports is primarily governed by the inertia of the fluid. Applying the law of conservation where the flow of the fluid into the electrode equals the flow of fluid out of the electrode, a significant amount of energy is used not only to pump the fluid to the tip electrode, but to provide the fluid with a desirable exit velocity from the electrode.

Another concern with conventional irrigated ablation tip electrodes is the axially variability of fluid mass flow rate through the tip electrode. Fluid entering a proximal end of a tip electrode chamber carries momentum in the axial direction such that more fluid tends to exit the fluid ports at the distal end compared to fluid ports on the radial side of the tip electrode. Such uneven distribution of fluid can cause undesirable "hot spots" which can compromise the size and quality of the lesions and require interruption of the ablation procedure so that coagulation can be removed from the tip electrode.

Ablation electrodes using a porous material structure can provide efficient coolant flow. The porous material in which tiny particles are sintered together to form a metallic structure provides a multiplicity of interconnected passages which allow for efficient cooling of an electrode structure. However, because the particles are sintered together, there can be concerns with particles detaching from the electrode and entering the bloodstream.

Irrigation tip ablation electrodes employing thin shells are known, where the shells have a plurality of irrigation fluid ports. The fluid ports are typically formed using sinker electrical discharge machining (EDM) technology. Although the sinker EDM process creates precise, minute geometries, it is typically an extremely slow process, with a single irrigation port taking upwards of five minutes to completely form.

Accordingly, it is desirable that a catheter be adapted for mapping and ablation with improved irrigation fluid flow by means of more efficient use of the space in the tip electrode that avoids the introduction of additional bonding joints. It is desirable that an irrigated tip electrode use provides an internal fluid path that has a better consideration and utilization of inherent fluid dynamics for improved fluid flow and cooling of the tip electrode. Moreover, it is desirable that irrigation ports be formed utilizing a more time and cost efficient process which would improve manufacturing capacity and also reduce unit cost.

SUMMARY OF THE INVENTION

The present invention is directed to a catheter adapted for mapping and ablating heart tissue with improved irrigation fluid flow into and out of the tip electrode. By considering and applying fluid characteristics and dynamics, the ablation tip electrode efficiently uses space and distributes fluid more uniformly and with higher velocity without necessarily using more power and energy at the irrigation fluid pump source or increasing fluid load on the patient.

In one embodiment, an irrigated ablation catheter includes an elongated catheter body, a deflectable section distal to the catheter body and an ablation tip electrode. The tip electrode has a two piece design comprising a thin outer shell defining a cavity, and an internal member that fits inside the shell. The shell has a predetermined plurality of fluid ports, each with a predetermined diameter and each contributing to a total fluid output area of the tip electrode. The internal member has a plug member and a baffle member. The plug member includes a fluid inlet into the cavity of the tip electrode where the fluid inlet has a predetermined cross-sectional shape defining a fluid input area. Moreover, the cavity is designed to function as a plenum chamber by providing a variable inner cross-section so that momentum of the fluid entering the chamber is diffused and axial variability of fluid mass flow rate through the tip electrode fluid ports is reduced.

In a more detailed embodiment, the catheter of the present invention has a tip electrode wherein the diffusion ratio of total fluid output area to fluid input area that is less than 2.0, and a fluid port ratio of tip electrode shell thickness to fluid port diameter that is less than 3.25. Moreover, the tip electrode also has a fluid inlet aspect ratio greater than 1.0 where the fluid inlet has a noncircular (for example, oval or elliptical) radial cross-section defined by a wider dimension along one axis and a narrower dimension along another axis. The plenum chamber has an inner flow contour, for example, a bottleneck, where a narrow proximal portion opens to a wider distal portion so that fluid pressure increases while axial fluid velocity decreases which decreases axial momentum for a more uniform distribution of fluid in the tip electrode and thus more uniform flow of fluid exiting the fluid port.

In a detailed embodiment, the internal member includes a distal baffle member and a proximal plug member connected by a stem. Distal ends of irrigation tubing, electrode lead wires, puller wires and thermocouple wires are anchored in the plug member. The plug has an inlet passage allowing the irrigation tubing to deliver fluid into the tip electrode. The inlet passage is off-axis and has a noncircular cross-sectional shape which efficiently uses the limited space in the tip electrode. The baffle member is shaped to diffuse fluid entering the tip electrode from the irrigation tubing as the fluid flows through the bottleneck of the plenum chamber. The baffle member is positioned on axis as it houses an electromagnetic position sensor advantageously in a centered distal position in the tip electrode. A cable for the sensor extends proximally from the sensor through a passage extending through the baffle member, the stem and the plug member.

As another feature of the present invention, the fluid ports have a tapered cylindrical configuration with divergent walls that are formed by laser drilling. Laser drilling offers advantages, including no consumable/degradable tools, when compared to traditional screw machine or sinker EDM processes. The absence of degradable tooling allows laser drilling to be a more efficient process, because in-process adjustment is not required to compensate for tool wear. Additionally, the laser cutting mechanism is orders of magnitude faster than a comparable EDM process, with a single fluid port being drilled in seconds.

The divergent walls of laser drilled fluid ports are a result of transverse modes present in the focused laser beam and its interaction with surrounding substrate material (namely, the shell). The degree of taper is relatively small, ranging between 0 and 6 degrees, but the taper advantageously provides an increase in volumetric flow rate and a decrease in hydraulic resistance.

In one embodiment, each fluid port has a tapered configuration, for example, a frustoconical configuration defined by a taper angle, with a smaller inlet diameter and a larger outlet diameter, where the smaller inlet diameter ranges between about 0.003 inch and 0.005 inch. The taper angle may range between about 0 degrees to 6 degrees. Thickness of the electrode shell may range between about 0.003 inch to 0.004 inch.

BRIEF DESCRIPTION OF THE DRAWINGS

These and other features and advantages of the present invention will be better understood by reference to the following detailed description when considered in conjunction with the accompanying drawings wherein:

FIG. 2C is an end cross-sectional view of the intermediate section of FIGS. 2A and 2B, taken along line 2C-2C.

FIG. 16 is a Regression Table for Irrigation Port Pressure Drop Model

FIG. 17 is a schematic representation of irrigated tip shell hydraulic as an electrical circuit.

FIG. 22 is a chart showing Bulk Hydraulic Resistance for various port configurations.

FIG. 23 is a graph correlating laser drilled port geometry to EDM port geometry.

DETAILED DESCRIPTION OF THE INVENTION

Figure 1:
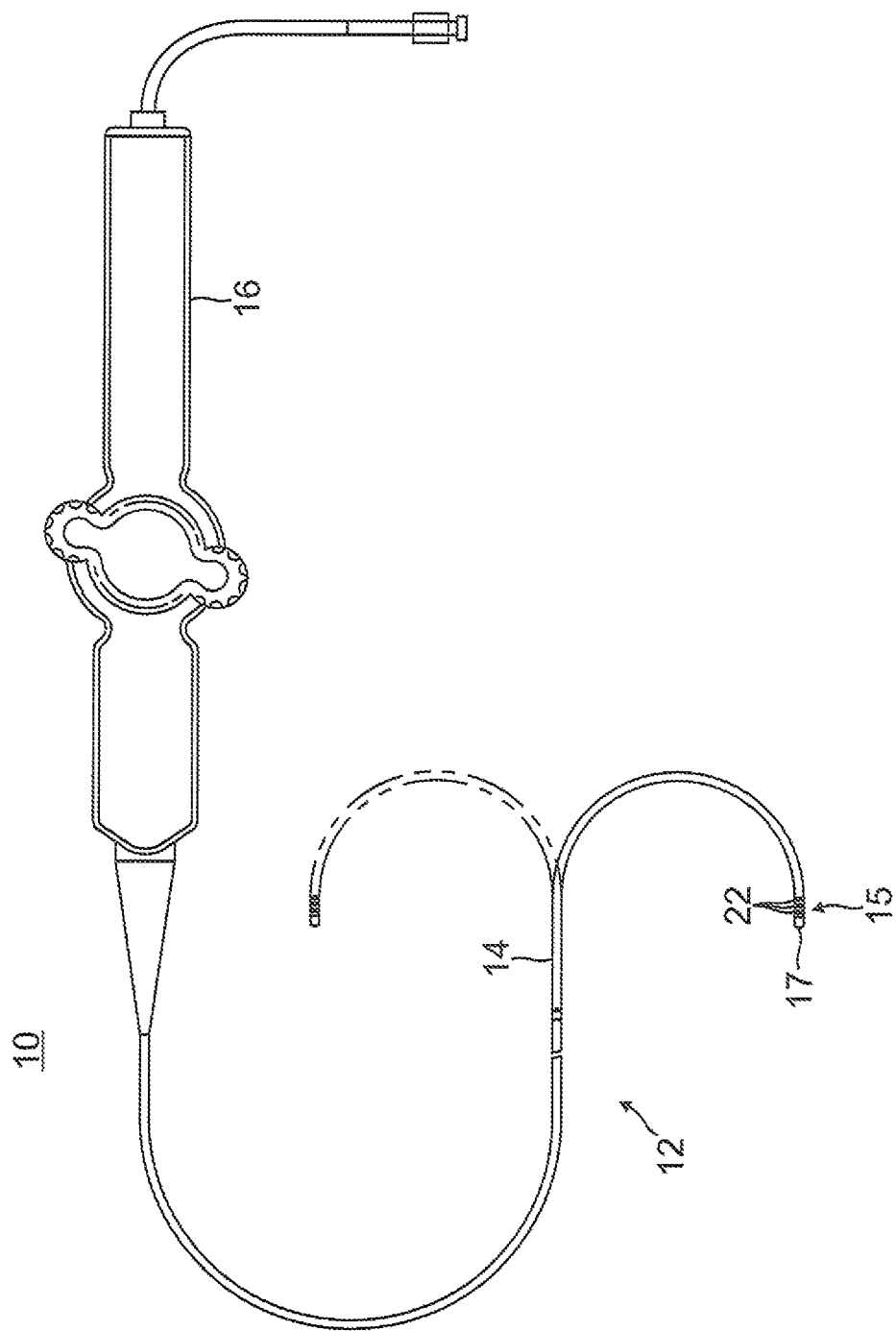
FIG. 1 is a side view of an embodiment of a catheter of the present invention.

FIG. 1 illustrates an embodiment of a catheter 10 with improved irrigation flow through a tip ablation electrode 17. The tip electrode is configured to promote fluid flow into the tip electrode and dispersion of fluid therein in providing more uniform fluid coverage and flow at all locations on the exterior of the tip electrode. The catheter is therefore operable at lower flow rates with lower fluid load on the patient while providing improved cooling of the tip electrode. Moreover, a high fluid exit velocity at the tip electrode provides a "jetting" action that aids in creating a fluid boundary layer around the tip electrode which reduces the occurrence rate of char and/or thrombus during ablation. Fluid, e.g., saline or heparinized saline, can be transported to the ablation site from the tip electrode to cool tissue, reduce coagulation and/or facilitate the formation of deeper lesions. It is understood that other fluids can be delivered, as well, including any diagnostic and therapeutic fluids, such as neuroinhibitors and neuroexcitors.

The catheter 10 has an elongated catheter body 12 with proximal and distal ends, an intermediate deflectable section 14 at the distal end of the catheter body 12, and a distal section 15 with the irrigated mapping and ablation tip electrode 17. The catheter also includes a control handle 16 at the proximal end of the catheter body 12 for controlling deflection (single or bi-directional) of the intermediate section 14.

Figure 2A:
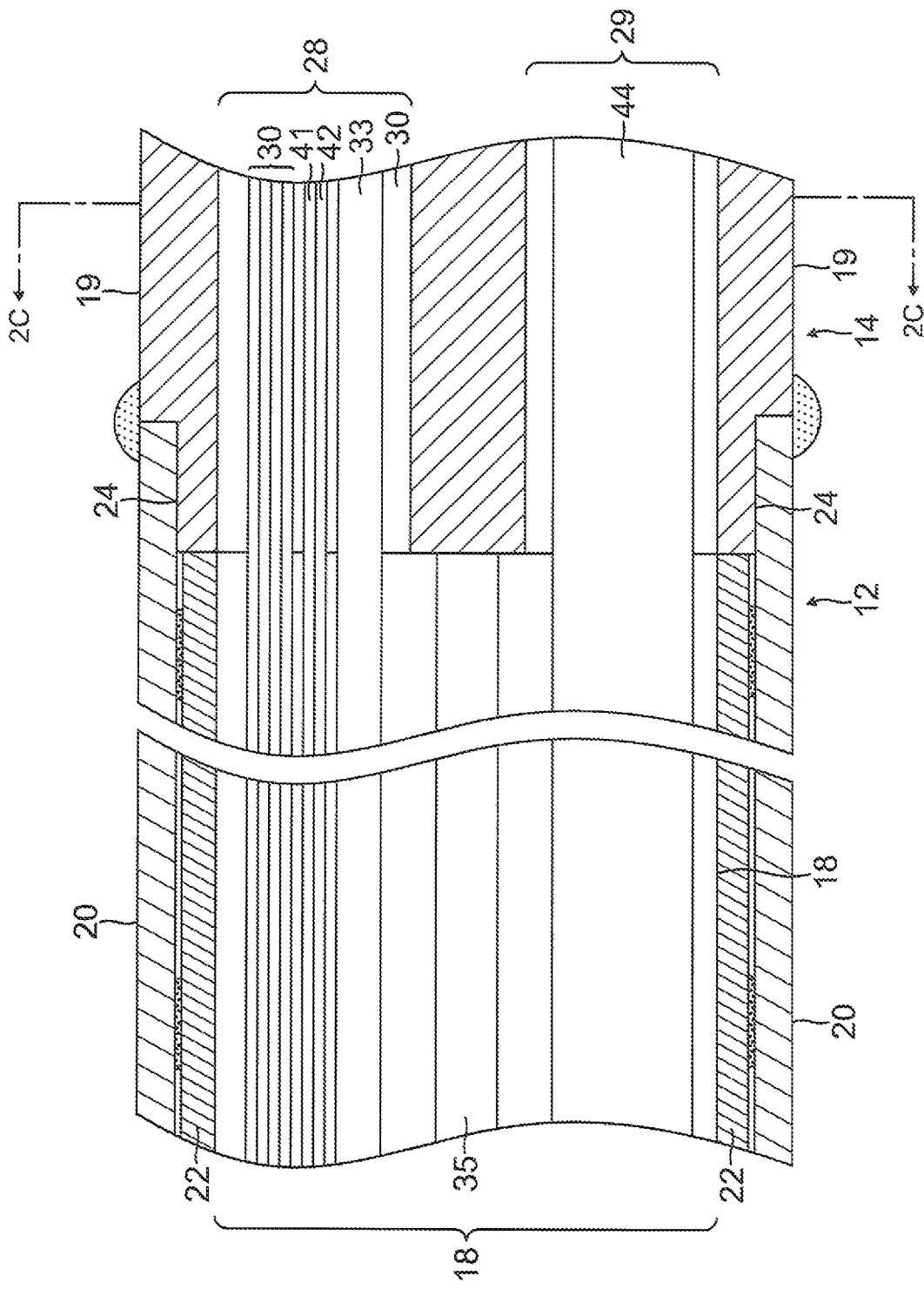
FIG. 2A is a side cross-sectional view of the catheter of FIG. 1, including a junction between a catheter body and a deflectable intermediate section, taken along a diameter.
Figure 2B:
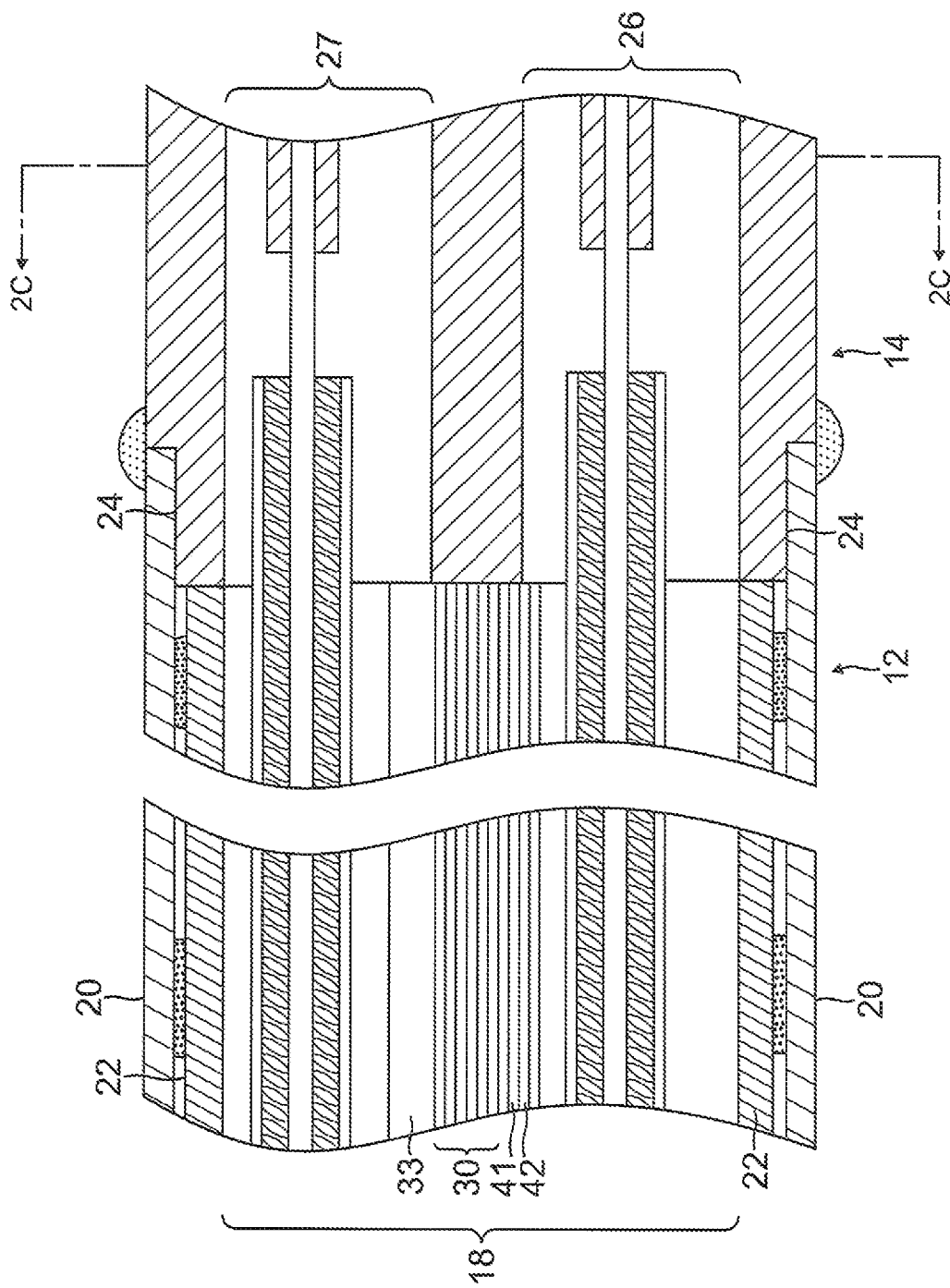
FIG. 2B is a side cross-sectional view of the catheter of FIG. 1, including a junction between a catheter body and a deflectable intermediate section, taken along a diameter generally orthogonal to the diameter of FIG. 2A.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate puller members (e.g., puller wires), lead wires, and any other desired wires, cables or tubings. If desired, the inner surface of the outer wall 20 is lined with a stiffening tube 22 to provide improved torsional stability. A disclosed embodiment, the catheter has an outer wall 20 with an outer diameter of from about 0.090 inch to about 0.94 inch and an inner diameter of from about 0.061 inch to about 0.065 inch.

Distal ends of the stiffening tube 22 and the outer wall 20 are fixedly attached near the distal end of the catheter body 12 by forming a glue joint 23 with polyurethane glue or the like. A second glue joint 25 is formed between proximal ends of the stiffening tube 20 and outer wall 22 using a slower drying but stronger glue, e.g., polyurethane.

Components that extend between the control handle 16 and the deflectable section 14 pass through the central lumen 18 of the catheter body 12. These components include lead wires 30 for the tip electrode 17 and ring electrodes 22 on the distal section 15, an irrigation tubing 38 for delivering fluid to the distal section 15, a cable 33 for a position location sensor 34 carried in the distal section, puller wire(s) 32 for deflecting the intermediate section 14, and a pair of thermocouple wires 41, 42 to sense temperature at the distal tip section 15.

Illustrated in FIGS. 2A, 2B and 2C is an embodiment of the intermediate section 14 which comprises a short section of tubing 19. The tubing also has a braided mesh construction but with multiple off-axis lumens, for example lumens 26, 27, 28 and 29. The first lumen 26 carries a puller wire 32 for deflection of the intermediate section. For bi-directional deflection, the diametrically opposing second lumen 27 can carry a second puller wire 32. The third lumen 28 carries the lead wires 30, the thermocouple wires 41 and 42, and the sensor cable 33. The fourth lumen 29 carries the irrigation tubing 38.

The tubing 19 of the intermediate section 14 is made of a suitable non-toxic material that is more flexible than the catheter body 12. A suitable material for the tubing 19 is braided polyurethane, i.e., polyurethane with an embedded mesh of braided stainless steel or the like. The size of each lumen is not critical, but is sufficient to house the respective components extending therethrough.

A means for attaching the catheter body 12 to the intermediate section 14 is illustrated in FIGS. 2A and 2B. The proximal end of the intermediate section 14 comprises an outer circumferential notch 23 that receives an inner surface of the outer wall 20 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Each puller wire 32 is preferably coated with Teflon® The puller wires can be made of any suitable metal, such as stainless steel or Nitinol and the Teflon coating imparts lubricity to the puller wire. The puller wire preferably has a diameter ranging from about 0.006 to about 0.010 inch.

As shown in FIG. 2B, portion of each puller wire 32 in the catheter body 12 passes through a compression coil 35 in surrounding relation to its puller wire. The compression coil 35 extends from the proximal end of the catheter body 12 to the proximal end of the intermediate section 14. The compression coil is made of any suitable metal, preferably stainless steel, and is tightly wound on itself to provide flexibility, i.e., bending, but to resist compression. The inner diameter of the compression coil is preferably slightly larger than the diameter of the puller wire. Within the catheter body 12, the outer surface of the compression coil 35 is also covered by a flexible, non-conductive sheath 39, e.g., made of polyimide tubing.

Proximal ends of the puller wires 32 are anchored in the control handle 16. Distal ends of the puller wires 32 are anchored in the distal section 15 as described further below. Separate and independent longitudinal movement of the puller wire 32 relative to the catheter body 12, which results in, respectively, deflection of the intermediate section 14 and distal section 15 along a plane, is accomplished by suitable manipulation of a deflection member of the control handle 16. Suitable deflection members and/or deflection assemblies are described in U.S. Publication Nos. 2010/0168827 and 2008/0255540, the entire disclosures of both of which are hereby incorporated by reference.

Figure 3:
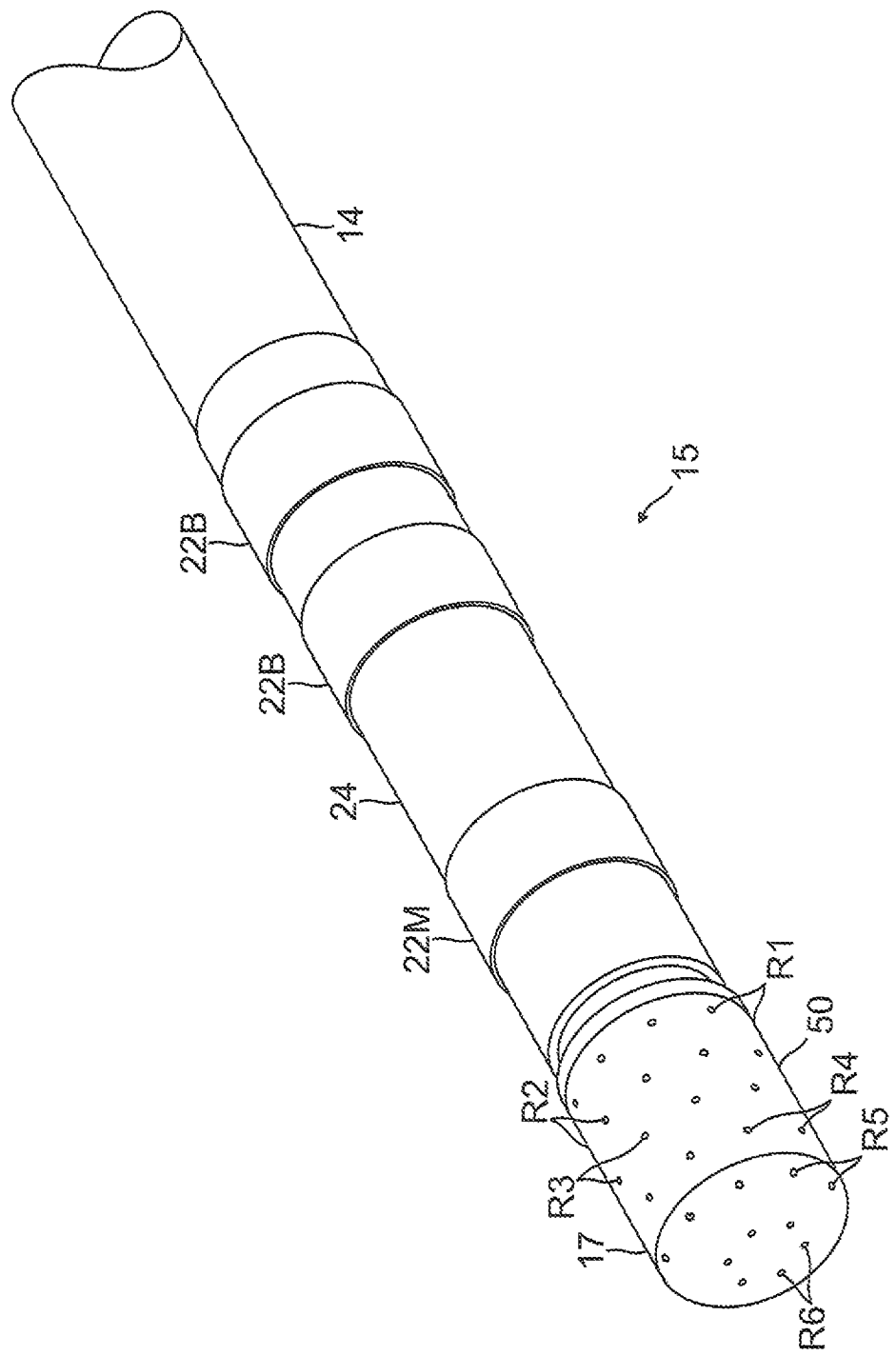
FIG. 3 is a perspective view of a distal section of the catheter of FIG. 1.
Figure 4:
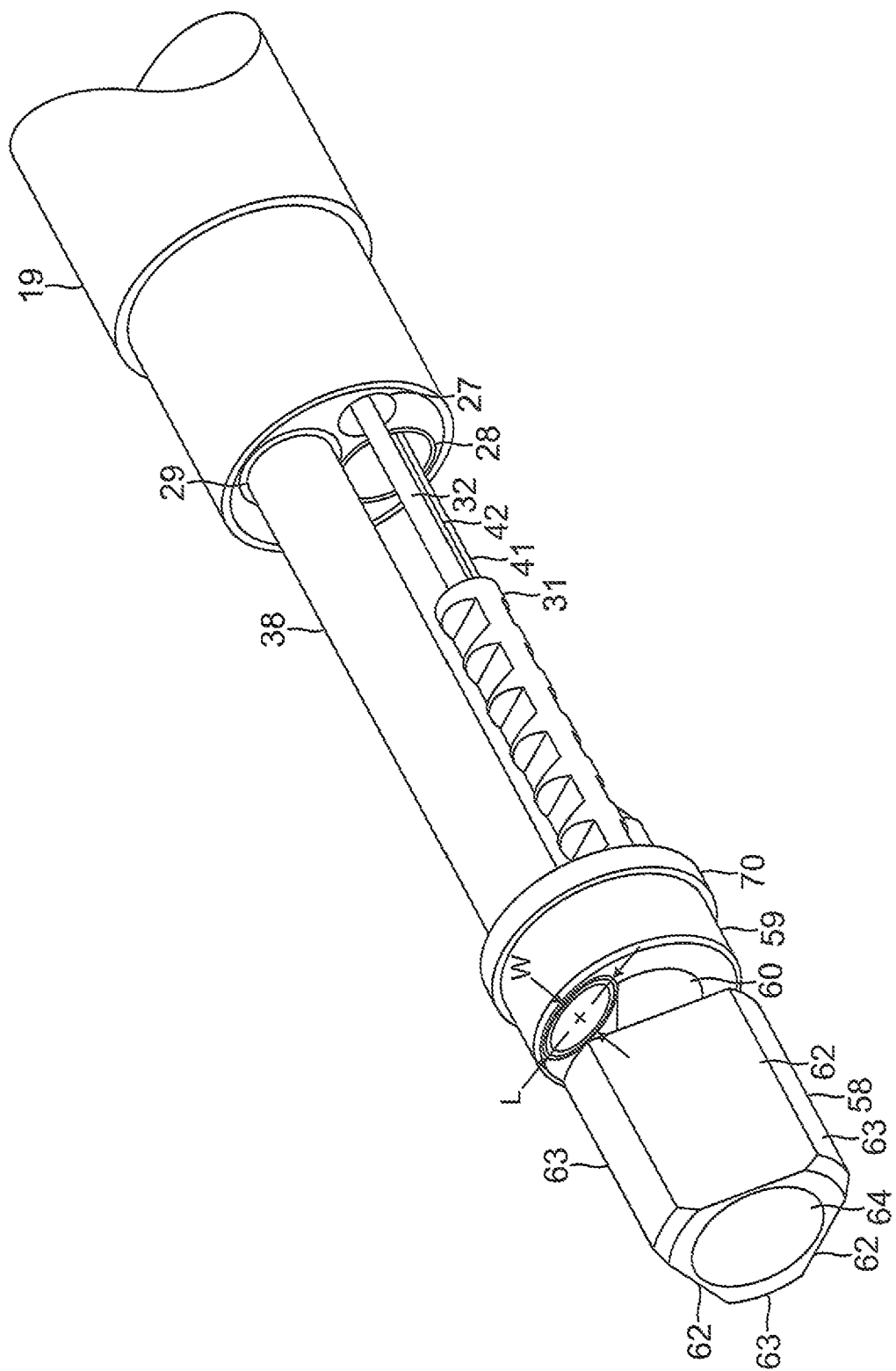
FIG. 4 is a perspective view of the distal section of FIG. 3, with selected components removed for better viewing of the interior of the distal section, including an embodiment of an internal member.

At the distal end of the intermediate section 14 is the distal tip section 15 that includes the tip electrode 17 and a relatively short piece of connection tubing or covering 24 between the tip electrode 17 and the intermediate section 14. In the illustrated embodiment of FIGS. 3 and 4, the connection tubing 24 has a single lumen which allows passage of the tip and ring electrodes lead wire 30, the sensor cable 33, thermocouple wires 41 and 42, the puller wires 32, and the irrigation tubing 38 into the tip electrode 17. The single lumen of the connection tubing 24 allows these components to reorient themselves as needed from their respective lumens in the intermediate section 14 toward their location within the tip electrode 17. In the disclosed embodiment, the tubing 24 is a protective tubing, e.g., PEEK tubing, having a length ranging between 6 mm and 12 mm, more preferably about 11 mm. It is noted that selected components, including the tip and ring electrode lead wires 30 are not shown for better clarity of other components and structure of the tip electrode.

Figure 3A:
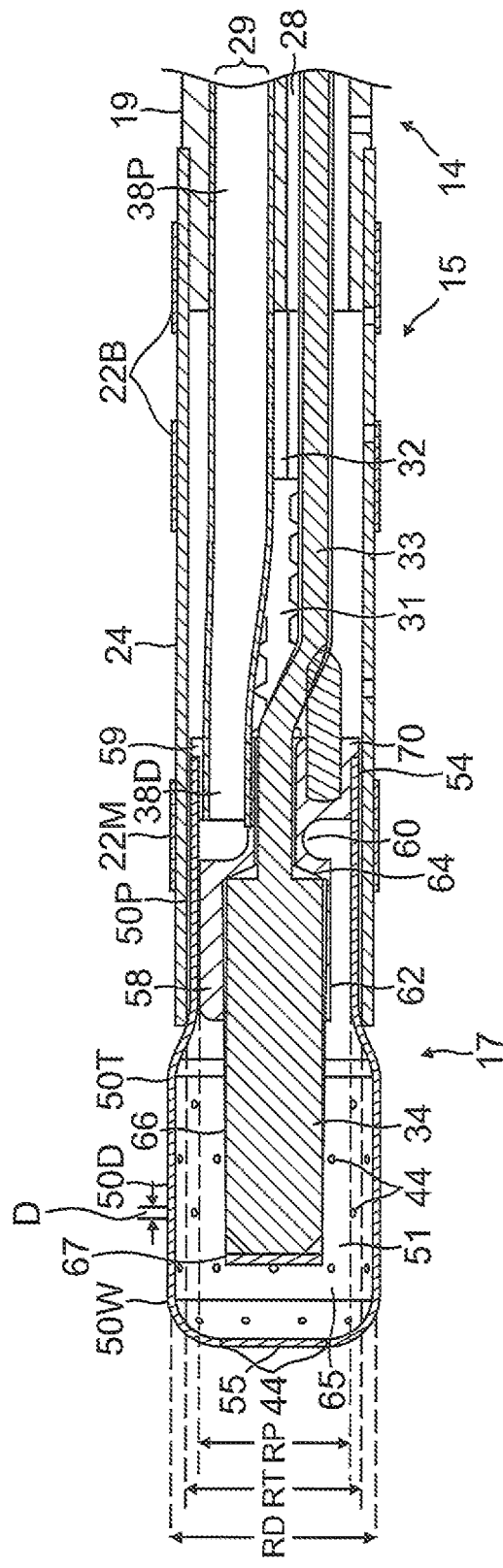
FIG. 3A is a side cross-sectional view of the distal section of FIG. 3, taken along a first diameter.
Figure 3B:
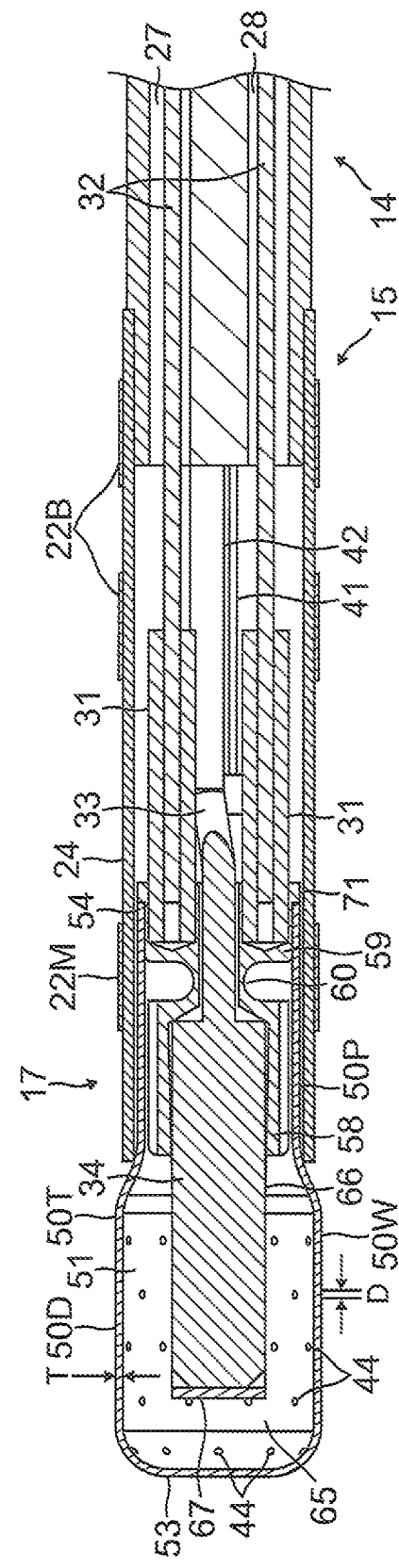
FIG. 3B is a side cross-sectional view of the distal section of FIG. 3, taken along a second diameter generally orthogonal to the first diameter.

Better seen in FIGS. 3A and 3B, the tip electrode 17 defines a longitudinal axis and is of a two piece configuration that includes an electrically conductive shell 50, an internal member 52 and a cavity or chamber 51 generally surrounded and enclosed by the shell and internal member. The shell is elongated, with a tubular or cylindrical shape. The shell has a closed and rounded atraumatic distal end 53 and an open proximal end 54 that is sealed by the internal member. In the illustrated embodiment, the shell is radially symmetrical where the radial cross section of the shell 50 is circular, but it is understood that the radial cross section may be any shape as desired. The shell has a distal portion 50D, a proximal portion 50P and a short tapered portion 50T therebetween connecting the two portions. The cavity 51 extends the length of the shell such that there is an inner dimension or radius RD in the distal portion 50D, an inner dimension or radius RT in the tapered portion 50T and an inner dimension or radius RP in the proximal portion 50P where the radii have the following relationships: RD>RP and RD>RT>RP. In the disclosed embodiment, RD is about 1.15 mm, RP is about 1.0 mm and RT is about 1.075 mm. A length of the shell from the distal end 53 to the proximal end 54 ranges between about 2 mm to 12 mm, and preferably between about to 3 mm to 10 mm, and more preferably about 7.5 mm.

The internal member 52 inside the proximal portion of the shell has a length that is about half of the length of the shell. The internal member is radially symmetrical and has a distal portion (or baffle member) 58 and a proximal portion (or plug member) 59 that are connected by a narrow on-axis stem 60. The baffle member has a greater length and the plug member has a lesser length. In the disclosed embodiment, internal member 52 is radially symmetrical and its length is about 3.0 mm to 4.0 mm with the length of the baffle member 58 being about twice the length of the plug member 59.

Figure 5:
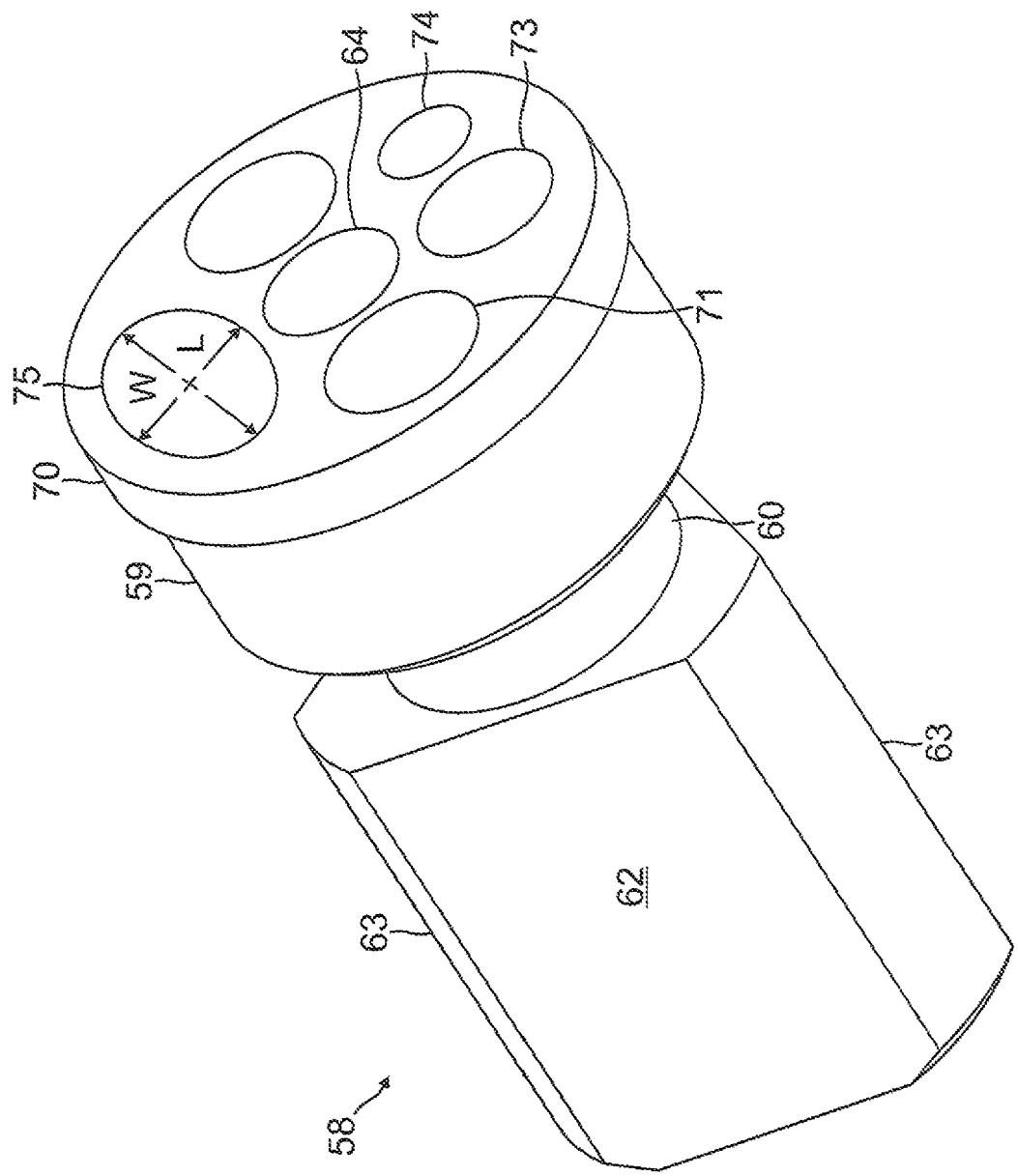
FIG. 5 is a perspective view of a proximal end of the internal member of FIG. 4.
Figure 6:
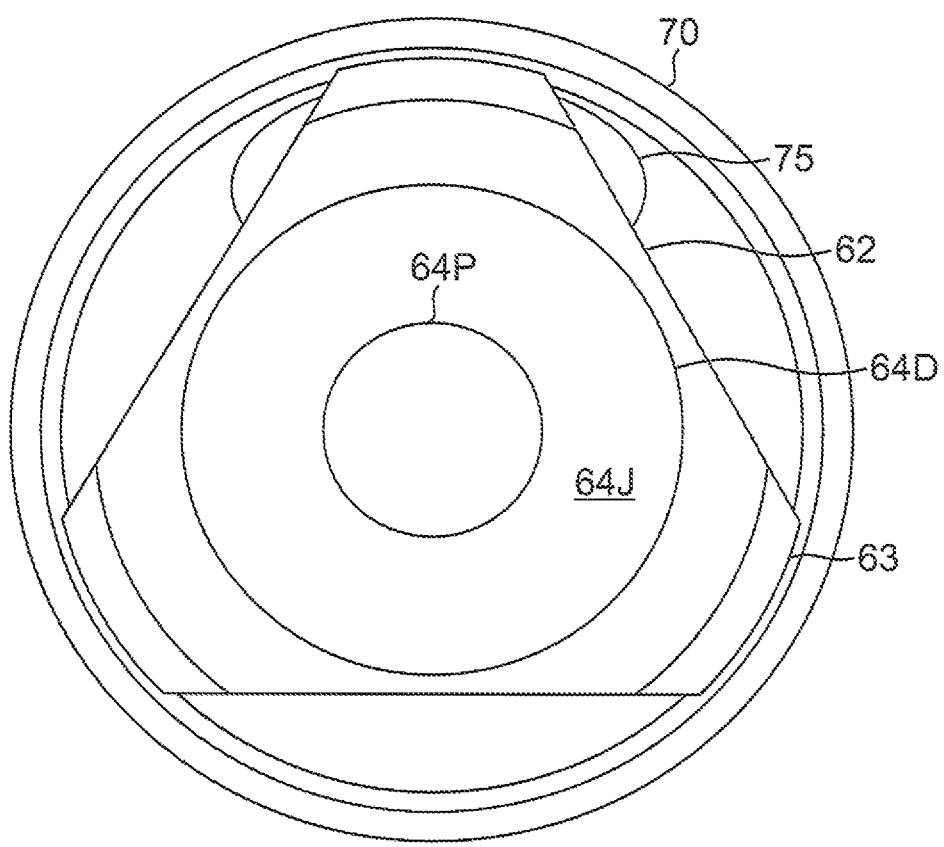
FIG. 6 is a distal end view of the internal member of FIG. 5.

With reference to FIGS. 5 and 6, the plug member 59 has a circular cross section that corresponds with the circular cross section of the proximal portion 50P of the shell 50 so that it forms a snug fit in providing a fluid-tight seal at the proximal end 54 of the tip electrode 17. The plug member 59 seals the interior cavity 51 of the shell 50, and the shell and the plug member facilitate the provision of a plenum condition within the cavity; that is, where fluid is forced or delivered into it for a more uniform distribution through fluid ports 44 formed in the shell, as discussed further below.

The baffle member 58 has a radial cross-section that is nonconforming to the inner radial cross section of the shell surrounding the baffle member, so that separate gaps or pathways are provided for fluid flowing through the tip electrode. In the disclosed embodiment, baffle member 58 has a polygonal cross-section, for example, a triangular cross-section as illustrated, with a plurality of angled baffles or generally flat surfaces 62. Truncated corners 63 between the surfaces are dimensioned for contact with inner surface of the shell wall. The internal member 52 has an on-axis passage 64 extending through the entirety of its length, including the baffle member 58, the stem 60 and the plug member 59. A distal portion 64D of the passage extending through the baffle member 58 houses a proximal portion of the position sensor 34. A proximal (and narrower) portion 64P of passage 64 extending through the stem 60 and the plug member 59 allows the sensor cable 33 to extend proximally from the sensor. A junction between the distal and proximal portion of the passage acts as a stop 64J abutting against the proximal end of the position sensor 34. In the disclosed embodiment, the length of the distal portion 64D of the passage is about half of the length of the position sensor 34. A distal portion of the sensor 34 is sealed and protected from surrounding fluid by a nonconducting, biocompatible tubing 66, e.g., polyimide tubing, whose distal end extends slightly beyond the distal end of the position sensor 34 and is sealed by a plug of sealant material 67. The distal end of the tubing 66 is proximal of the distal end 53 of the shell 50 so there is a space or gap 65 for fluid to circulate and reach the distal end of the shell.

The stem 60 of the internal member 52 has a generally circular radial cross-sectional shape, with a diameter slightly greater than the diameter of the passage 64P. Its small diameter allows fluid exiting the irrigation tubing 38 to impinge on the proximal surface of the baffle member 58, circulate and better fill the chamber 51 of the tip electrode before flowing distally.

On a proximal end of the plug member 59, a circumferential lip 70 is formed. With the tip electrode 17 assembled, the proximal end 54 of the shell 50 abuts a distal surface of the lip. The lip prevents the shell 50 from being installed improperly over the internal member 52. In particular, the lip ensures the gap 65 between the distal ends of the baffle member and the shell, while the truncated corners of the baffle member ensure axial alignment between the shell and the internal member. A distal portion of the connection tubing 24 extends over the lip 70 and the proximal portion 50P of the shell 50 such that a distal end of the tubing 24 is at or near the tapered portion 50T of the shell.

On a proximal surface of the plug member 59, blind holes 71, 73 and 74 are provided. A distal end of each puller wire 32 is anchored in holes 71 by means of a ferrule 31 as known in the art. Distal end of tip electrode lead wire 30 is anchored in hole 74, and distal ends of thermocouple wires 41, 42 are anchored in hole 73. As mentioned, the on-axis through-passage 64 houses the sensor 34 and the cable 33. Another through-passage, for example, an off-axis through-passage 75, is provided in the plug member 59 to receive a distal end of the irrigation tubing 38 which feeds fluid into the enclosed chamber 51 of the tip electrode 17. In accordance with a feature of the present invention, the through-passage 75 has a predetermined cross-sectional shape that efficiently uses the limited space on the proximal surface of the plug member 59. That is, the tip electrode 17 including the internal member 52 considers a fluid inlet aspect ratio Ratio$_{INLET}$, as defined by Equation (1) below:

$$\text{Ratio}_{INLET} = L/W \qquad \text{Eqn (1)}$$

where:

L is a greater (or length) dimension;

W is a lesser (or width) dimension; and

In particular, the plug member 59 has an irrigation inlet passage radial cross-section wherein the ratio Ratio$_{INLET}$ is limited to being greater than or equal to 1.0, per Equation (2), and preferably not greater than 10 as per Equation (2a) as follows:

$$\text{Ratio}_{INLET} \geq 1 \qquad \text{Eqn (2)}$$

Figure 7:
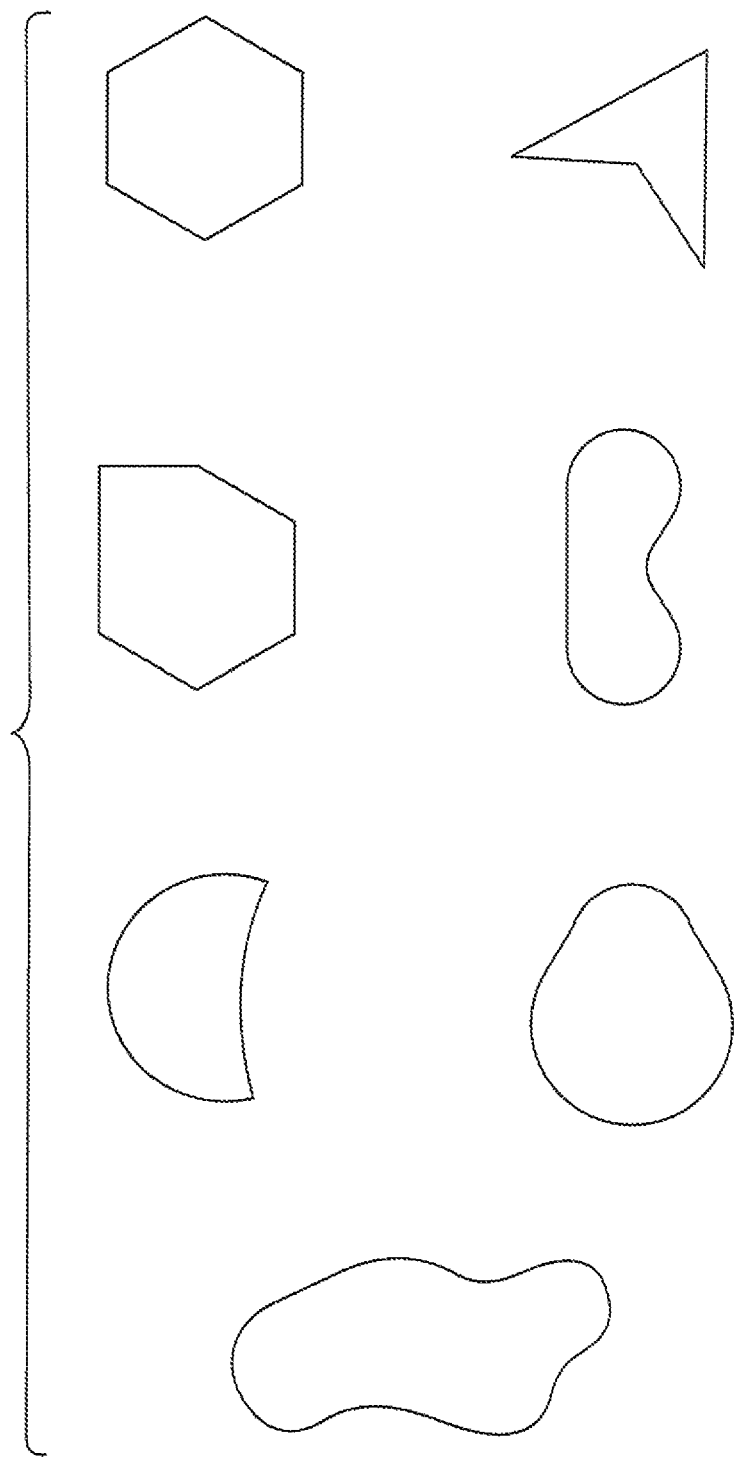
FIG. 7 illustrate various noncircular shapes.

In the illustrated embodiment, the oval or elliptical cross-sectional shape of the fluid inlet passage 75 is defined by Equations (1) and (2), including but not limited to where the dimensions are generally orthogonal to each other. Although the illustrated embodiment is an oval or ellipse, it is understood that the present invention is directed to an irrigation inlet with any noncircular shapes, including irregular circles, regular or irregular polygons, and "ameobic" shapes, for example, kidney-bean, crescent, peanut, hourglass, and pear shapes, as shown in FIG. 7. The noncircular cross-sectional shapes that can be assumed by the passage can also be formed by combinations of a plurality of two or more irrigation tubings 38 in contact and/or close proximity. Indeed, a bundle of irrigation tubings can be inserted into the inlet passage 75 so long as the passage is effectively sealed at its proximal end, for example, by means of a funnel seal or sleeve. In fact, a large number of different noncircular shapes is subject only to the layout and arrangement of the other components in the tip electrode, means of manufacturing the plug member in forming the inlet passage and/or means of sealing the irrigating tubing(s) to the inlet passage. The present invention recognizes that a noncircular cross-section shape uses space within the tip electrode more efficiently than a circular shape. Irrigation tubing(s) constructed of flexible material, e.g., polyimide, can readily adapt to the shape of the through-passage allowing the tubing(s) to be continuous without the need for bond joints along their length. As illustrated in FIG. 3B, a continuous irrigation tubing 38 is used, at least through the distal section 15. Its flexibility and elasticity allow different cross sections along its length. A distal portion 38D of the tubing extending generally within the connection tubing 24 has a cross section and size similar to that of the irrigation through-passage 75. A portion 38P proximal the connection tubing 24 has a more conventional circular cross-section.

The shell 50 is constructed of a biocompatible metal, including a biocompatible metal alloy. A suitable biocompatible metal alloy includes an alloy selected from stainless steel alloys, noble metal alloys and/or combinations thereof. In one embodiment, the shell is constructed of an alloy comprising about 80% palladium and about 20% platinum by weight. In an alternate embodiment, the shell is constructed of an alloy comprising about 90% platinum and about 10% iridium by weight. The shell can formed by deep-drawing manufacturing process which produces a sufficiently thin but sturdy shell wall 50W that is suitable for handling, transport through the patient's body, and tissue contact during mapping and ablation procedures. In a disclosed embodiment, the shell wall 50W has a generally uniform thickness T ranging between about 0.003 in and 0.010 in, preferably between about 0.003 in and 0.004 in, and more preferably about 0.0035 in. While the deep drawn method is well suited to manufacturing the shell with a sufficiently thin wall, it is understood that other methods, such as drilling and/or casting/molding, can also be used.

With the shell wall sufficiently thin, an electrical discharge machining (EDM) process can be employed to form a plurality of fluid ports or orifices 44 in the shell wall 50W of the distal portion 50D that allow fluid communication between the chamber 51 and outside the shell. In a disclosed embodiment, the plurality of ports 44 ranges between about 20 and 96, preferably between about 30 and 60, more preferably about 56. A diameter D of each fluid port ranges between about 0.003 in. and 0.007 in., preferably between about 0.003 inch and 0.004 inch, and more preferably about 0.0035 inch.

In the disclosed embodiment, there are 56 ports, arranged in six circumferential rows, where five rows R1-R5 have 10 ports each, and a distal row R6 has six ports. The ports of rows R1-R5 are generally equidistant from each other, although the ports of adjacent rows are offset from each other such that each port is equidistant to four or six adjacent ports. A most distal ten-port row R5 is located at the rounded distal portion of the shell. The row (or circle) R6 is on a flat or nearly flat distal end 53 of the shell. The six ports of the row R6 are equi-angular on the circle.

In accordance with another feature of the present invention, the tip electrode 17 including the shell 50 has a configuration that considers a fluid port ratio Ratio$_{PORT}$ as defined by Equation (3) below:

$$\text{Ratio}_{PORT} = T/D \qquad \text{Eqn (3)}$$

where:

T = thickness of shell wall; and

D = diameter of a fluid port

In particular, the tip electrode of the present invention has the fluid port aspect ratio Ratio$_{PORT}$ being less than 3.25 as per Equation (4) below, preferably less than or equal to about 1.5 as per Equation (5), and more preferably less than or equal to about 1.0, as per Equation (6) below:

$$\text{Ratio}_{PORT} < 3.25 \qquad \text{Eqn. (4)}$$

$$\text{Ratio}_{PORT} \leq 1.5 \qquad \text{Eqn. (5)}$$

$$\text{Ratio}_{PORT} \leq 1.0 \qquad \text{Eqn. (6)}$$

Such a thin shell configuration with fluid ports 44 of a predetermined diameter D, including where the shell wall thickness T is less than the fluid port diameter D, fosters a fluid flow through the tip electrode that can be characterized as thin plate orifice flow which operates by a distinct set of characteristics, as discussed below.

Equation (7) below is an expression of Bernoulli's law based on the principle of conservation of energy (pressure and kinetic energy only when applying the assumption of a common flow height such that potential energy can be ignored):

$$\frac{P_{OUT}}{\rho} + \frac{V_{OUT}^2}{2} = \frac{P_{IN}}{\rho} + \frac{V_{IN}^2}{2} + \frac{\Delta P_{OUT-IN}}{\rho} \qquad \text{Eqn. (7)}$$

Where:

$P_{OUT}$ = discharge ambient pressure outside tip electrode $P_{IN}$ = upstream pressure at distal end of irrigation tubing inside tip electrode $\Delta P_{OUT-IN}$ = pressure loss in fluid port $V_{OUT}$ = velocity outside the tip electrode $V_{IN}$ = velocity inside the tip electrode $\rho$ = density Applying the assumption that pressure loss in the fluid port is low to negligible (pressure drop is included with coefficient of discharge), and expressing velocities $V_{OUT}$ and $V_{IN}$ in terms of flow rate and diameter, per Equations (8) and (9) below:

$$V_{OUT} = \frac{4Q}{\pi D_{OUT}^2} \qquad \text{Eqn (8)}$$

$$V_{IN} = \frac{4Q}{\pi D_{IN}^2} \qquad \text{Eqn (9)}$$

where:
Q=volumetric flow rate
$D_{IN}$=theoretical diameter leading into the fluid port, estimated by separation distance between adjacent fluid ports
$D_{OUT}$=diameter of fluid port
the pressure drop through the fluid can be expressed as Equation (10) below:

$$\frac{P_{IN} - P_{OUT}}{\rho} = 1/2\{(16Q^2/\pi^2 D_{OUT}^4) - (16Q^2/\pi^2 D_{IN}^4)\} \qquad \text{Eqn (10)}$$

Because the fluid port is small compared to the spacing between the fluid ports, where $D_{IN}$ is much greater than $D_{OUT}$, Equation (10) can be simplified to Equation (11) below, which shows that as the diameter of the fluid port increases, the hydraulic resistance decreases by the fourth power.

$$\Delta P = P(8Q^2)/(\pi^2 D_{OUT}^4) \qquad \text{Eqn (11)}$$

Another feature of the present invention is the tip electrode considers a diffusion $\text{Ratio}_{DIF}$, as shown in Equation (12) below:

$$\text{Ratio}_{DIF} = A_{OUTPUT}/A_{INPUT} \qquad \text{Eqn. (12)}$$

where:
$A_{OUTPUT}$ is the total area of all fluid ports of the shell
$A_{INPUT}$ is the area of the irrigation tubing distal end inlet In particular, the tip electrode configuration of the present invention limits the diffusion $\text{Ratio}_{DIF}$ to less than about 2.0 per Equation (13a), preferably less than about 1.8 per Equation (13b), and more preferably less than about 1.3 per Equation (13c) below:

$$2.0 > \text{Ratio}_{DIFFUSION} \qquad \text{Eqn (13a)}$$

$$1.8 > \text{Ratio}_{DIFFUSION} \qquad \text{Eqn (13b)}$$

$$1.3 > \text{Ratio}_{DIFFUSION} \qquad \text{Eqn. (13c)}$$

Bernoulli's law of Equation (7) above assumes that the fluid is incompressible and suffers no friction as it moves through a pipe. In reality, velocity varies throughout the fluid depending on the viscosity of the fluid. For sufficiently small velocities, such as those through irrigated catheters, the flow is generally laminar, i.e. layered. With laminar flow, velocities vary parabolically across a pipe with a circular cylindrical cross section. As the velocity increases past a critical value, depending upon the viscosity and density of the fluid, eddies appear and the flow becomes turbulent.

The laminar flow through a pipe is described by the Hagen-Poiseuille law, per Equation (14) below which states that volume of fluid flowing per unit time is proportional to the pressure difference $\Delta P$ between the ends of the pipe and the fourth power of its radius r:

$$Q = \frac{\pi \Delta P r^4}{8 \eta L} \qquad \text{Eqn. (14)}$$

Where:
Q=volume of fluid flowing per unit time
$\Delta P$=pressure difference between the ends of the pipe
r=radius of the pipe
L=length of the pipe
$\eta$=dynamic viscosity, a characteristic of a given fluid By solving for $\Delta P$, Equation (14) can be expressed with the change in pressure as a function of flow rate and radius, as per Equation (15) below:

$$\Delta P = \frac{8Q\eta L}{\pi r^4} \qquad \text{Eqn. (15)}$$

Thus, an increase in the radius results in a significant decrease in pressure change, and vice versa. And, because hydraulic resistance $R_H$ is a function of viscosity and the geometries of the pipe, as per Equation (16) below, an increase in radius results in a significant decrease in hydraulic resistance, and vice versa:

$$R_H = \frac{8nL}{\pi r^4} \qquad \text{Eqn. (16)}$$

In the present invention, the shell of the tip electrode advantageously capitalizes on the inverse dependency between change in pressure and fluid port radius, and between hydraulic resistance and fluid port radius by utilizing a thin tip electrode shell wall 50W with a predetermined plurality of fluid ports 44. Because of the relatively small thickness T of the shell wall (taken to be the "length L" in Eqn (16)), the fluid ports can be readily manufactured in a variety of sizes and radius (taken to be the "radius r" in Eqn (16)) such that the fluid port ratio is less than 3.25 per Eqn (4) above, preferably less than about 1.5 per Eqn (5), and more preferably less than about 1.0 per Eqn (6). As the fluid port ratio approaches or becomes less than 1.0, the fluid flow through the ports can be characterized as "thin plate orifice flow." Moreover, with a predetermined plurality of fluid ports of a predetermined radius or diameter, the diffusion ratio of a total output area (e.g., number of ports in tip electrode shell multiplied by area of each port) to input area (e.g., cross-sectional area of inlet 75) can be readily determined and limited to being less than 2.0 per Eqn (13a), preferably less than 1.8 per Eqn (13b), and more preferably less than about 1.3 per Eqn (13c). By reducing the diffusion ratio, the flow of irrigation fluid is largely governed by back pressure of the fluid within the tip electrode. And, because total mass flow rate of the fluid in and out the tip electrode must conserved per Equation (7) above, a reduced total output area is advantageously compensated for by higher fluid velocities at the fluid ports in creating "jetting action" at the tip electrode.

In accordance with yet another feature of the present invention, the tip electrode 17, and in particular, the shell 50 and the chamber 51, have a variable internal cross section with a larger distal inner radial dimension or cross section in the distal portion 50D and a smaller proximal inner radial dimension or cross section in the proximal portion 50P, with the tapered section 50T facilitating the transition of the changing inner radial dimension therebetween. The tapered section may be at or near a midpoint along a length of the shell as illustrated but it can also be closer to either the distal end or the proximal end. While an outer radial dimension of the shell along its length may be variable or not, it is the variable inner radial dimension along the length of the electrode that advantageously affects fluid flow and creates desirable turbulence within the chamber to provide a plenum condition.

In keeping with Eqn (7), the expansion or increase in chamber volume from the bottleneck formation of the proximal portion 50P widening to the distal portion 50D increases pressure and decreases velocity in the fluid flowing distally in the tip electrode. A plenum chamber effect is created which diffuses the momentum of the fluid, especially the axial component of the momentum. As the momentum or the irrigating fluid is diffused, axial variability of fluid mass flow rate through the tip electrode fluid ports 44 is reduced. The overall effect of this phenomenon is a more uniform irrigation fluid coverage and flow throughout the chamber of the tip electrode and thus at all locations on the exterior of the tip electrode via the ports 44.

Figure 8:
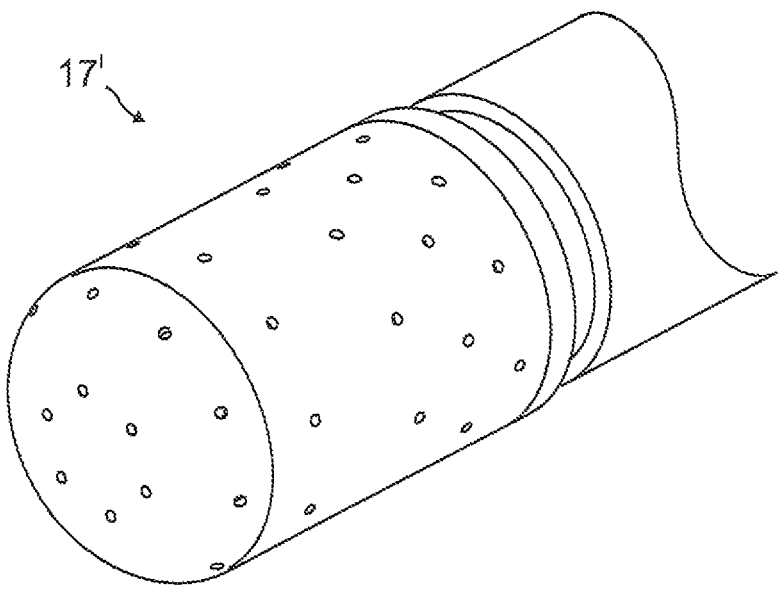
FIG. 8 is a perspective view of an alternate embodiment of a tip electrode of the present invention.
Figure 9:
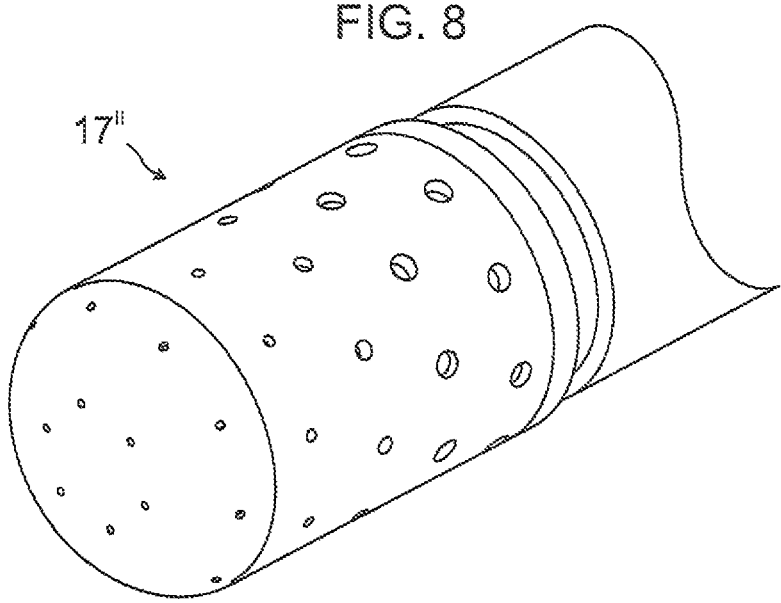
FIG. 9 is a perspective view of another alternate embodiment of a tip electrode of the present invention.

As understood by one of ordinary skill in the art, the tip electrode provides an internal geometry that controls irrigation fluid flow axial variation. However, the present invention includes an alternate embodiment wherein the density of fluid ports 44 (including the plurality of ports per unit area of the shell wall or surface) down the length of tip electrode 17' is varied, as shown in FIG. 8. Additionally, another alternate embodiment as shown in FIG. 9 provides a shell wherein the diameter of the ports varies axially along the length of a tip electrode 50'', including decreasing diameters toward the distal end. In either case, the effective fluid output area varies with the length of the tip electrode and compensates for the pressure drop in order to yield more uniform mass flow rates.

The ring electrodes 21 which are mounted on the connection tubing 24 can be made of any suitable solid conductive material, such as platinum or gold, preferably a combination of platinum and iridium. The ring electrodes can be mounted onto the connection tubing 24 with glue or the like. Alternatively, the ring electrodes can be formed by coating the tubing 24 with an electrically conducting material, like platinum, gold and/or iridium. The coating can be applied using sputtering, ion beam deposition or an equivalent technique. The number of the ring electrodes on the tubing 24 can vary as desired. The rings may be monopolar or bi-polar. In the illustrated embodiment, there is a distal monopolar ring electrode and a proximal pair of bi-polar ring electrodes. Each ring electrode is connected to a respective lead wire 30R.

Each lead wire 30R is attached to its corresponding ring electrode by any suitable method. A preferred method for attaching a lead wire to a ring electrode involves first making a small hole through the wall of the tubing 24. Such a hole can be created, for example, by inserting a needle through the non-conductive covering and heating the needle sufficiently to form a permanent hole. The lead wire is then drawn through the hole by using a microhook or the like. The end of the lead wire is then stripped of any coating and welded to the underside of the ring electrode, which is then slid into position over the hole and fixed in place with polyurethane glue or the like. Alternatively, each ring electrode is formed by wrapping a lead wire 30R around the non-conductive tubing 24 a number of times and stripping the lead wire of its own insulated coating on its outwardly facing surfaces.

The tip electrode 17 is electrically connected to a source of ablation energy by the lead wire 30T. The ring electrodes 21 are electrically connected to an appropriate mapping or monitoring system by respective lead wires 30R.

The lead wires 30T and 30R pass through the lumen 28 of the tubing 19 of the deflectable intermediate section 14 and the central lumen 18 of the catheter body 12. The portion of the lead wires extending through the central lumen 18 of the catheter body 12, and proximal end of the lumen 28 can be enclosed within a protective sheath (not shown), which can be made of any suitable material, preferably polyimide. The protective sheath is anchored at its distal end to the proximal end of the intermediate section 14 by gluing it in the lumen 28 with polyurethane glue or the like. Each electrode lead wire has its proximal end terminating in a connector at the proximal end of the control handle 16.

The tip electrode of the present invention can operate at about 8 ml/minute or lower for wattage below 30 and about 17 ml for wattage between 30 and 50. The reduction in fluid-loading on the patient in a five or six hour procedure can thus be very significant. Moreover, where the flow rate is regulated by a programmable pump, the flow rate can even be lower for lower wattage.

Figure 10:
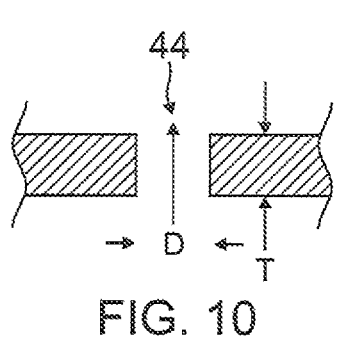
FIG. 10 is a side cross-sectional view of a fluid port with a right circular cylindrical configuration with straight and parallel walls.

With reference to FIG. 10, a fluid port 44 with a right circular cylindrical configuration is shown with diameter D ranging between about 0.003 and 0.005 inch and shell thickness T ranging between about 0.003 and 0.004 inch. The fluid port is manufactured with sinker EDM technology. A tungsten electrode is progressively plunged into shell wall to form individual irrigation ports by electrical erosion. With a straight, circular electrode, a right circular cylindrical irrigation port is formed with straight and parallel walls. This process is repeated multiple times over the shell to form the desired plurality of ports.

Figure 11:
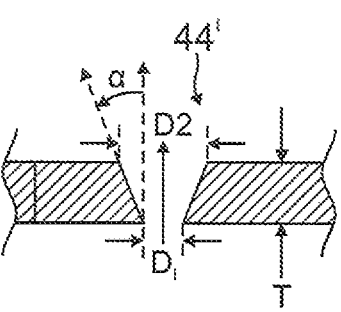
FIG. 11 is a side cross-sectional view of a fluid port with a tapered cylindrical configuration with divergent walls.

With reference to FIG. 11, a fluid port 44' with a tapered circular cylindrical or a frustoconical configuration, where an angle of taper a ranges between about 0 to 10 degrees, and preferably between about 4 to 6 degrees. In one embodiment, inner/inlet port diameter D1 ranges between about 0.003 inch and 0.004 inch, and outer/outlet port diameter D2 ranges between about 0.004 and 0.005 inch and shell thickness T ranges between about 0.003 inch and 0.004 inch. In accordance with a feature of the present invention, the taper angle α has a beneficial effect on irrigation port flow, as described below.

With reference to FIG. 11, a study with the following parameters was conducted which demonstrated the effect of taper angle on irrigation port flow:
Port Diameter D between 0.003 inch and 0.005 inch
Shell Thickness T between 0.003 inch and 0.004 inch
Bulk volumetric flow rate F between 8 ml/min and 15 ml/min
Taper Angle α of 0 to 6 degrees Saline flow through a fluid port 44 can be theoretically modeled through application of Bernoulli's equation. With the assumptions of steady-state incompressible flow and negligible frictional losses, Bernoulli's equation reduces to:

$$\dot{Q} = \frac{C_d}{\sqrt{1 - \left(\frac{d_2}{d_1}\right)^4}} A_2 \sqrt{\frac{2(\Delta P)}{\rho}} \qquad \text{Eqn (17)}$$

Figure 12:
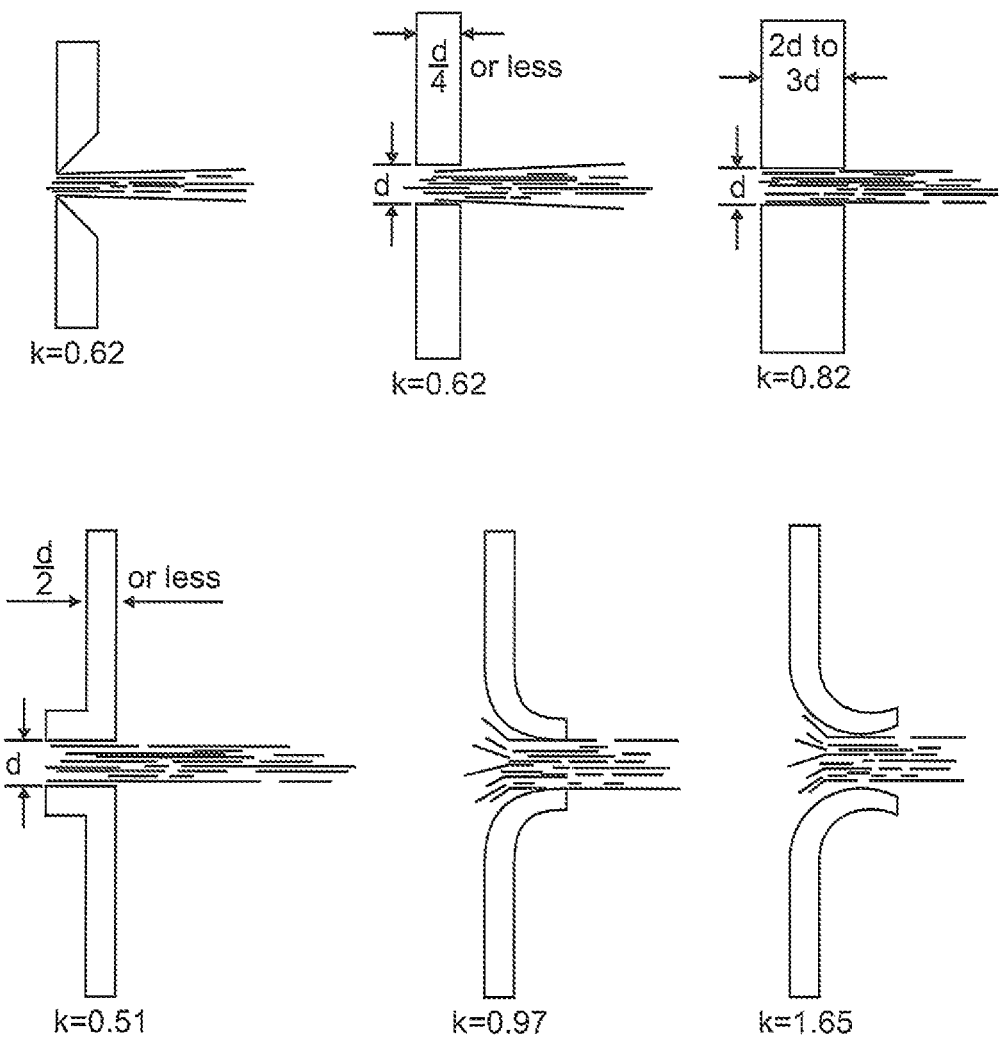
FIG. 12 is a Table of Standard Discharge Coefficients.

Where:
- Q̇ is volumetric flow rate through the port
- $C_d$ is the discharge coefficient
- $A_2$ is the area of the irrigation part
- $d_2$ is the diameter of the irrigation pod
- $d_1$ is the upstream diameter (assumed to be port to port spacing on irrigated tip)
- ΔP is the pressure drop across the irrigation port
- ρ is the fluid density Where the EDM and the laser drilling are centered with identical interior/inlet port diameters, the inputs to Bernoulli's equation (Eqn. 17) are identical. The effect of the taper angle is therefore manifested in different discharge coefficients $C_d$. The discharge coefficient for a given port can be approximately determined by referencing various fluid mechanics tables as shown in FIG. 12. Therein, it can be seen that taper angle, inlet radiuses, and the ratio of wall thickness to port diameter all effect $C_d$=1 being in perfect correlation with Bernoulli's equation. As such, standardized tables should be used with caution as their validity is heavily dependent on geometry and fluid conditions.

Figure 13:
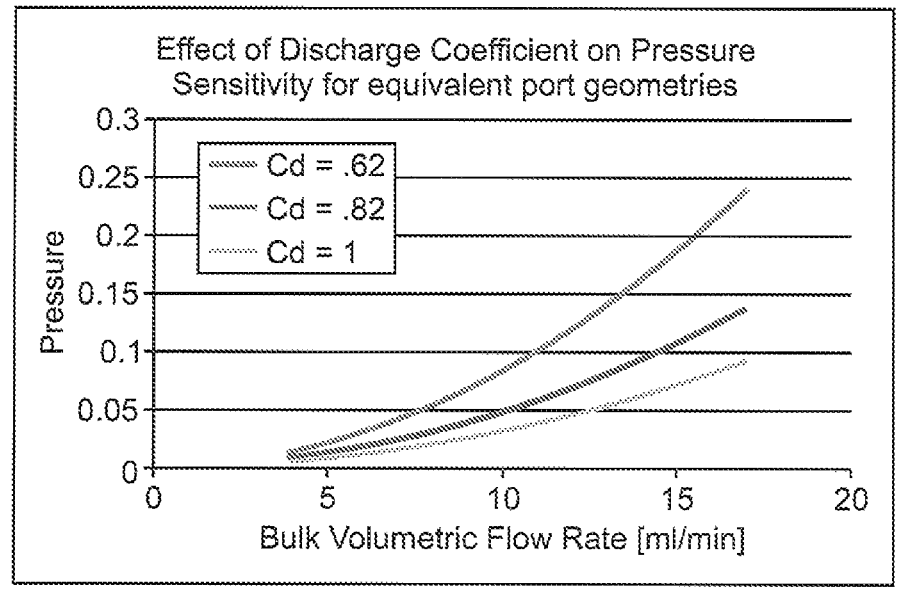
FIG. 13 is a graph showing Discharge Coefficient effect on Pressure versus Volumetric Flowrate Sensitivity.

In general, if the assumption is made that all over variables with the exception of Cd are constant between straight and tapered nozzles, Bernoulli's equation can be reduced to:

$$\Delta P = \frac{\dot{Q}^2}{C_d^2 M} \quad \text{Eqn (18)}$$

Where M is a proportionality constant based upon common port geometry. Plotting Eqn (18) yields a family of curves whose sensitivity is inversely proportional to $C_d^2$, see FIG. 13. The plot illustrates that it is not possible to fully characterize an irrigation port's flow performance without empirical verification of the discharge coefficient $C_d$.

Figure 14:
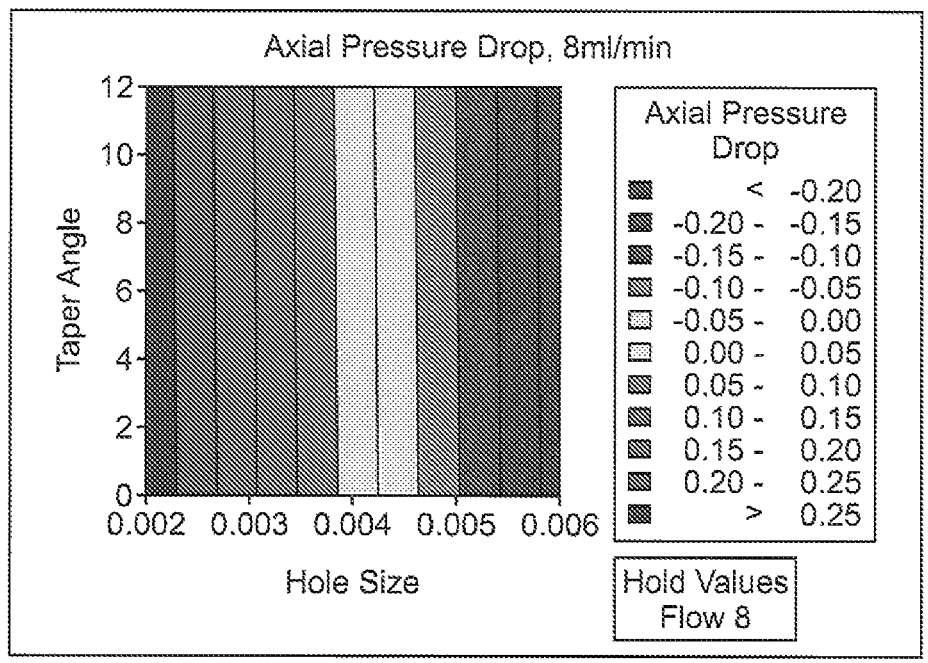
FIG. 14 is a graph showing Computational Fluid Dynamic of Irrigation Port Pressure Drop Sensitivity at 8 ml/min.
Figure 15:
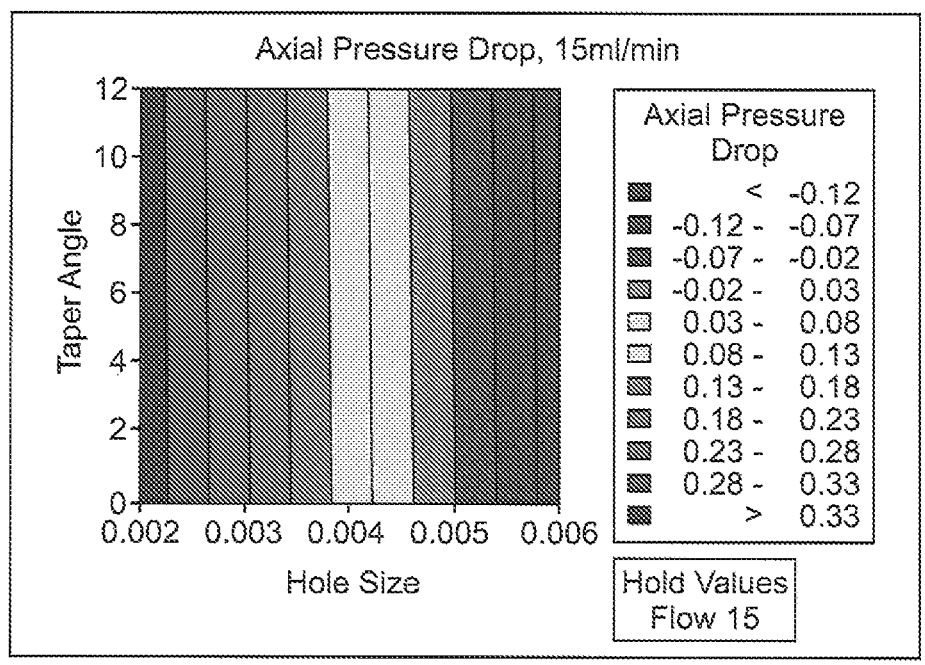
FIG. 15 is a graph showing Computational Fluid Dynamic of Irrigation Port Pressure Drop at 15 ml/min.

An alternate approach to theoretical modeling is to use computational numerical methods. A computational fluid dynamic (CFD) analysis was performed on fluid flow through a single fluid port over varying diameters, taper angles, and volumetric flow rates. The results of the multiple CFD runs were loaded into Minitab in a response surface DOE model in order to efficiently view the experimental space as shown in FIGS. 14, 15 and 16. A central composite DOE design was utilized to generate the CFD run combinations. The final response plots were generated using linear fits. In these plots, at both 8 ml/min and 15 ml/min volumetric flow rate, the effect of taper angle is minimal even at 12 degrees. Using the linear, multi-variable function generated in FIG. 16, the pressure drop for straight fluid port 44 (FIG. 10) and tapered fluid port 44' (FIG. 11) can be estimated at less than 5% difference.

ΔP=−0.000712(Taper Angle)−126.3(Port Diameter)+ 0.0104(Flow Rate)+0.456

| Port Diameter [in] | Flow Rate [ml/min] | Taper Angle | Pressure Drop [psi] | % change from 0° |
|---|---|---|---|---|
| 0.0035 | 15 | 0° | 0.170 | NA |
|  |  | 6° | 0.166 | 2.5% reduction |
|  |  | 12° | 0.161 | 5.0% reduction |

Furthermore, the Regression Table of FIG. 16 shows a P value of 0.938 for Taper Angle, indicating that it has little to no statistical significance and therefore has minimal effect on axial pressure drop relative to flow rate and inlet port diameter.

As discussed above, wall thickness of the tip electrode shell, and thereby the "length" of fluid port conduit affects the flow through the port. Because of the inability to precisely predict Cd, an alternate approach would be to characterize the port's total hydraulic resistance RH. Hydraulic resistance will effectively quantify the ration of force required to move a unit volume of fluid through the port. In order to characterize RH for the fluid port, it is convenient to consider an electric circuit analog. A simple resistor circuit can be constructed, which is analogous to the bulk fluid flow through the irrigated tip shell as shown in FIG. 17.

Using Ohm's Law, the electrical circuit resistance of FIG. 17 can be expressed as a function of voltage V and current i, as follows:

$$R = \frac{V}{i} \quad \text{Eqn (19)}$$

Similarly, the resistance RH of the hydraulic "circuit" above can be expressed in terms of pressure head P and volumetric flow rate Q as:

$$R_H = \frac{P}{\dot{Q}} \quad \text{Eqn (20)}$$

Figure 18:
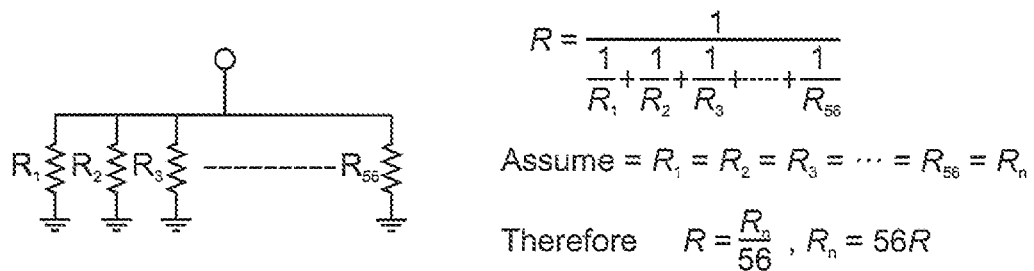
FIG. 18 is a schematic representation of the irrigated tip shell with 56 fluid ports as a parallel resistant network analog.

Eqn (20) addresses the resistance of 56 fluid ports of the irrigation ablation tip electrode together. However, with the assumption that all ports are approximately the same size and therefore the same resistance, the individual resistance of each port may be derived using a parallel resistance network analog, as shown in FIG. 18. The electrical resistance of an individual resistor can then be expressed as $$R_n = \frac{56\,V}{i} \quad \text{Eqn (21)}$$

By the same argument, the hydraulic analog may likewise be expressed as:

$$R_{H_n} = \frac{56P}{\dot{Q}} \quad \text{Eqn (22)}$$

Using the above relationship, the hydraulic resistance of a given port geometry may be quantitatively characterized by measuring the pressure head P at the inlet to the tip electrode and the result bulk volumetric flow rate Q.

Figure 19:
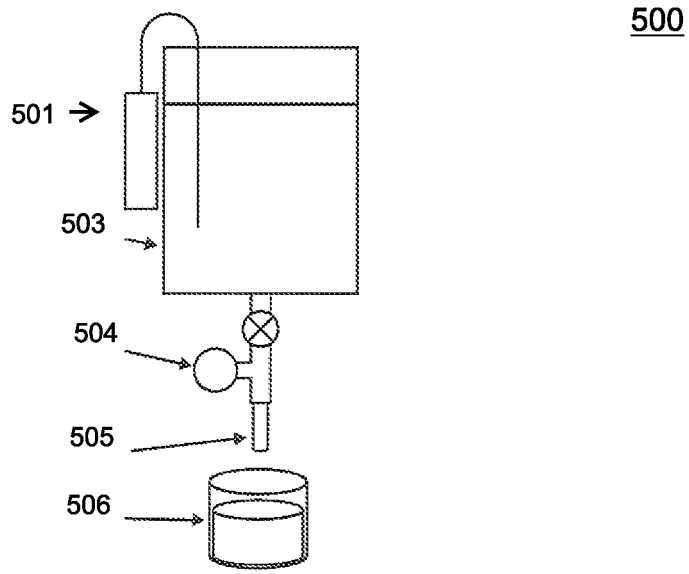
FIG. 19 is a diagram of a flow fixture for characterizing hydraulic resistance.

With reference to FIG. 19, a flow fixture 500 was developed to quantitatively measure hydraulic resistance $R_{Hn}$ for various irrigated tip shells. The flow fixture 500 includes a thermocouple 501, a water pressure head 502 (comprising a water tank 503, a pressure gage (ref. verification) 504 and a tip shell 505) and a collection beaker 506. Pressure P within the tip shell 505 is precisely controlled via the head height. Pressure is related to head height via the following equation:

$$P = \rho(T)gh \quad \text{Eqn (23)}$$

where ρ is water density, g is the local gravitational constant, and h is the height of the water column in the water tank 503 above the tip shell 505. Water density ρ is a function of temperature T which is monitored via the thermocouple on the water tank 503.

Volumetric flow rate $\dot{Q}$ is calculated by capturing fluid flow from the tip shell 505 into the beaker 506 over a period of time Δt. The net mass of the water $m_{net}$ is determined by weighing the filled collection beaker 506 and subtracting its dry mass. Volumetric flow rate is then calculated as shown below:

$$\dot{Q} = \frac{m_{net}}{\rho(T)\Delta t} \quad \text{Eqn (24)}$$

Hydraulic resistance $R_{H_n}$ of an individual port can then be calculated as:

$$R_{H_n} = \frac{56\rho^2(T)gh\Delta t}{m_{net}} \quad \text{Eqn (25)}$$

Figures 20, 21:
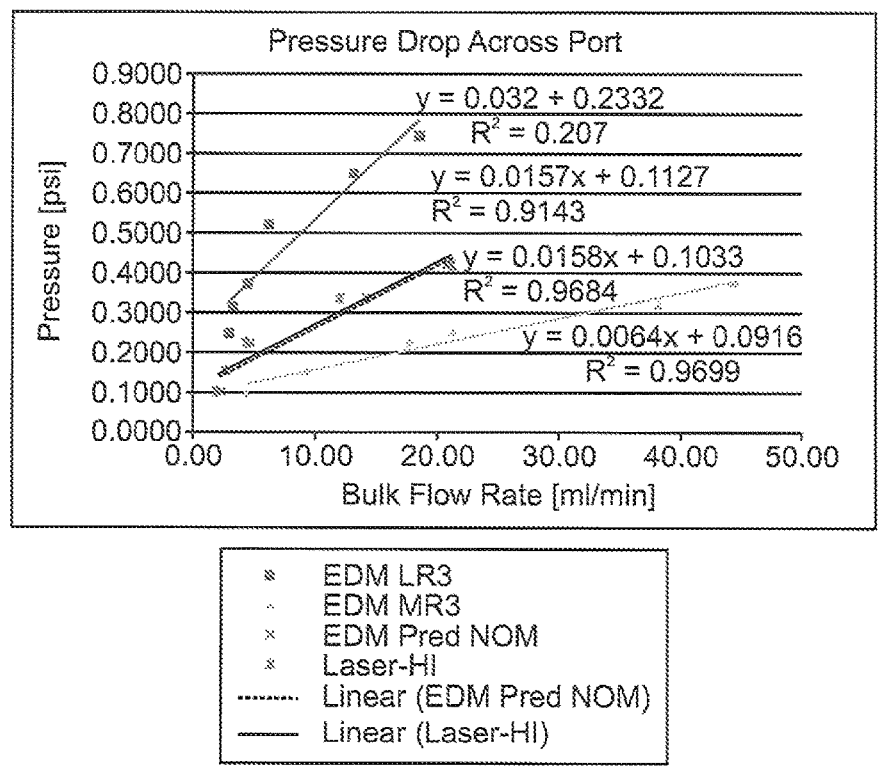
FIG. 20 is a chart showing summary of results of various port configurations characterized by the flow fixture of FIG. 19.
FIG. 21 is a graph showing Pressure versus Bulk Volumetric Flowrate

Tip shells with various port configurations were first dimensionally characterized on a Scanning Electron Microscope (SEM). Results are summarized in FIG. 20. Following dimensional characterization, each sample was tested on the flow fixture 500. Volumetric flow rate was recorded for each pressure head level setting as shown in FIG. 21. From the linear regressions in FIG. 21, the bulk hydraulic resistance RH for each tip shell can be calculated. Hydraulic resistance $R_{H_n}$ for each port is therefore equal to $56R_H$, as shown in FIG. 22.

In order to understand the effect of taper angle, the laser drilled port geometry sample is correlated to the EDM Nominal-Production port geometry sample as shown in FIG. 23. The correlation plot indicates that for the same pressure head, the laser drilled port geometry sample has a slightly lower volumetric flow rate, and is therefore more resistive. However, the areas of the EDM port and the laser drilled port are different, with the laser drilled port having a smaller, more restrictive area.

Figures 24, 25:
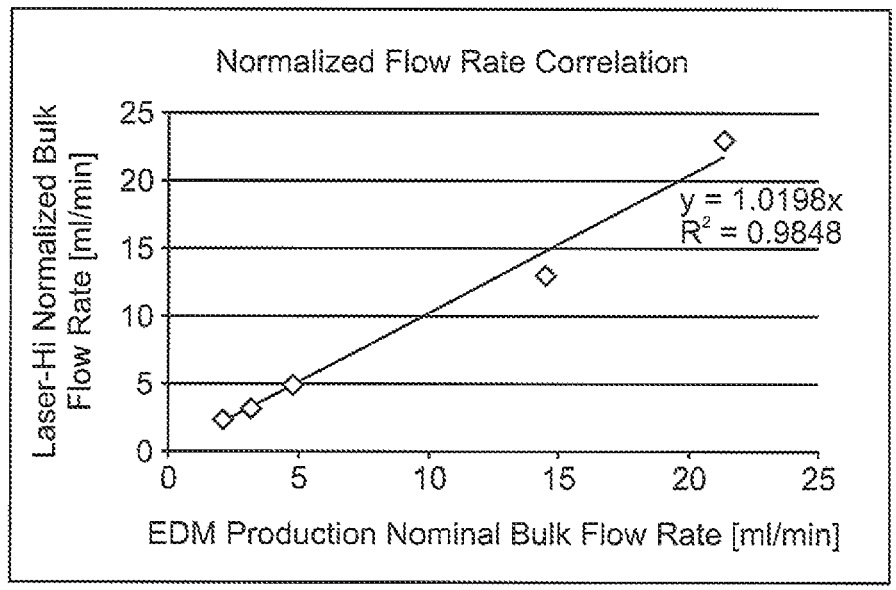
FIG. 24 is the graph of FIG. 23 with normalized flow rate.
FIG. 25 is a chart showing ranges of hydraulic resistance of a single EDM port.

Normalizing the data between the EDM sample and the laser sample to a nominal 0.0035 inch inlet port diameter (and therefore total area), and thereby eliminating the effect of surface area on port resistance exposes the hydraulic resistance component due to the 6 degree taper angle, as shown in FIG. 24. In the plot, of FIG. 24, the slope of the correlation line is 1.0198, which indicates that the laser drilled port has increased volumetric flow rate when compared to an EDM tip with the same port diameter at the same pressure head. The effect of the 6 degree taper angle is the different between the 1.0198 slope and an ideal correlation of 1.0.

$$\Delta\% = 100 \times \left(\frac{1.0198 - 1.0}{1.0}\right) = 1.98\% \quad \text{Eqn (26)}$$

Therefore the effect of the 6 degree taper angle is a 1.98% increase in volumetric flow rate, and conversely, a 1.98% decrease in hydraulic resistance.

Figure 26:
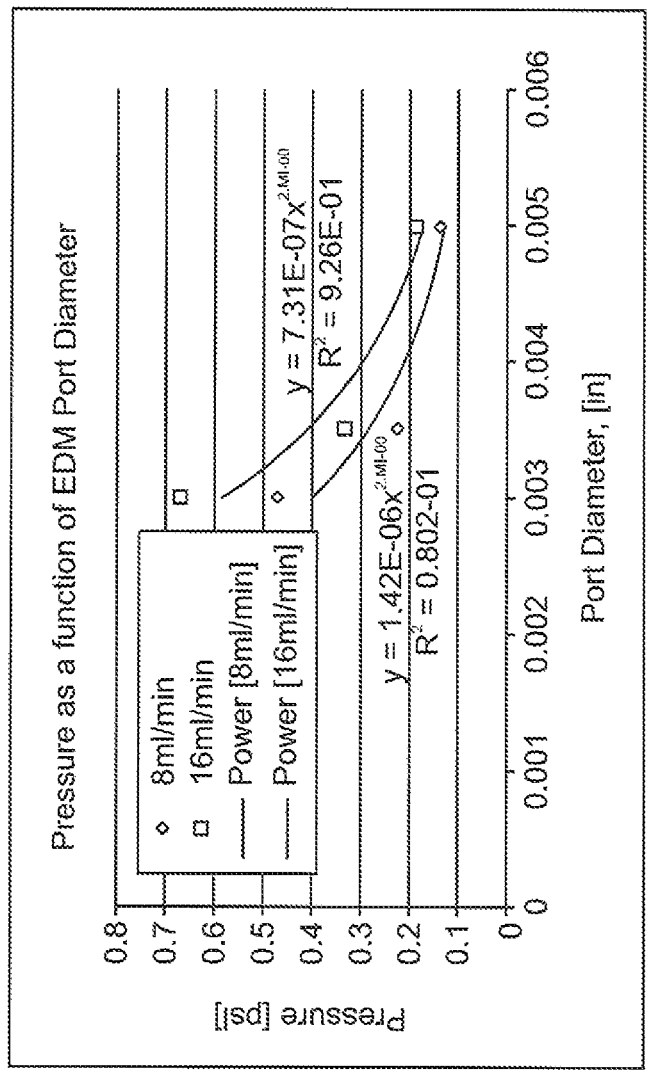
FIG. 26 is a graph showing diameter-based interpolation of EDM port pressure.
Figures 27, 28:
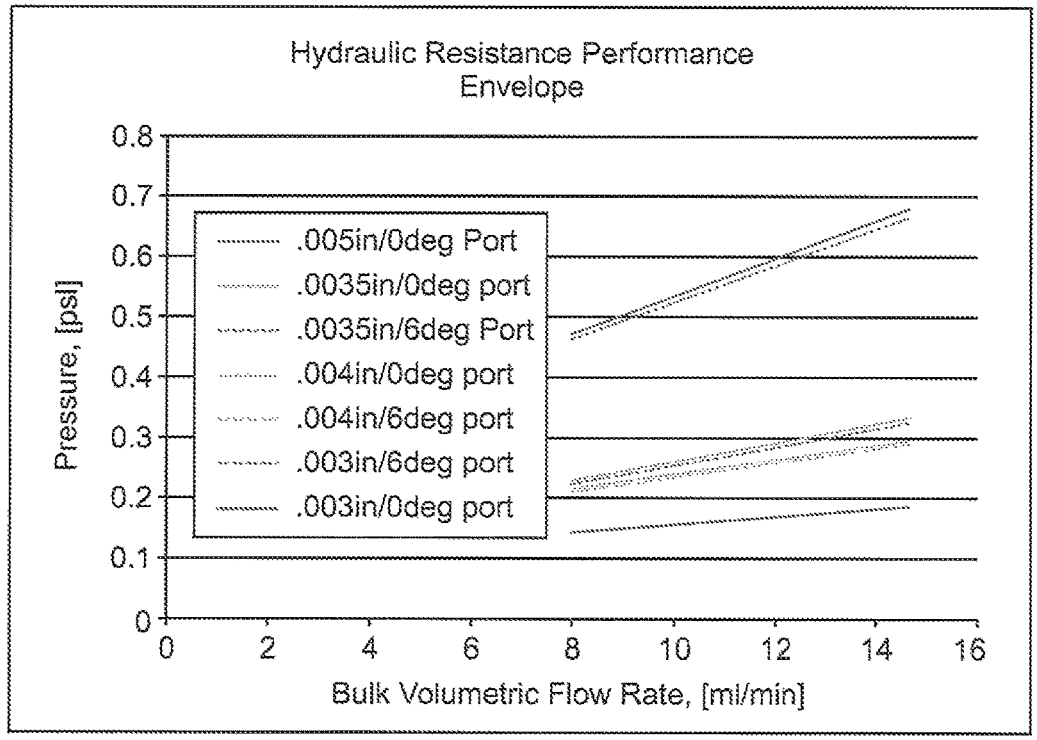
FIG. 27 is a graph showing hydraulic resistance performance envelope for EDM and laser drilled ports.
FIG. 28 is a chart showing hydraulic resistance of laser-drilled ports relative to validated specification limits.
Figure 29:
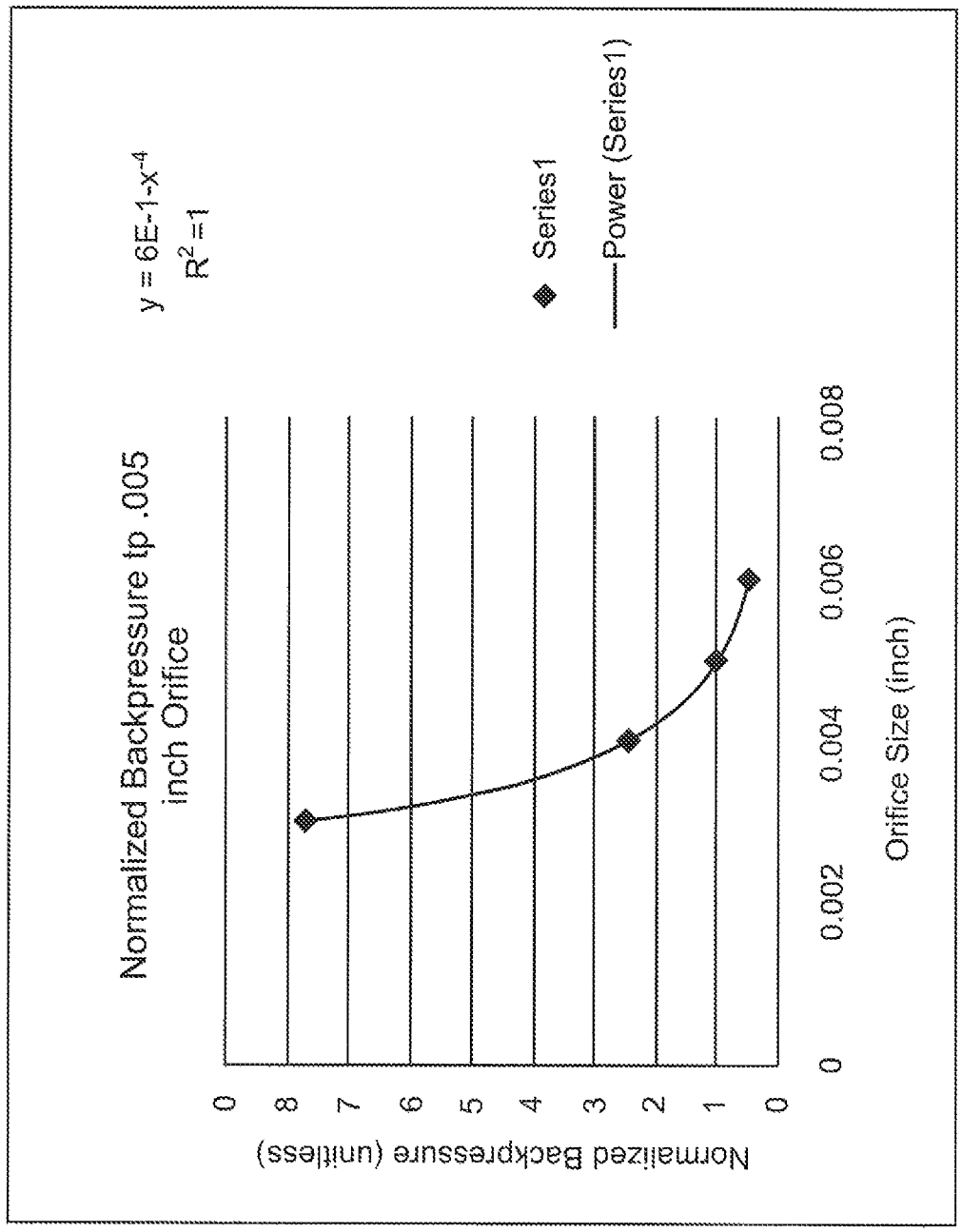
FIG. 29 is a graph showing the sensitivity of hydraulic resistance relative to a fluid port ("orifice") diameter of 0.005 inch.

The ranges of hydraulic resistance of a single irrigation EDM on ThermoCool SF Irrigated Tip Shell M-5787-03 as tested are shown in the Table of FIG. 25. With referenced to FIG. 26, an exponential fit was utilized to interpolate for the hydraulic resistance of an EDM tip with an 0.004 inch diameter port based upon the explicitly tested EDM configurations of 0.003 inch, 0.0035 inch and 0.005 inch diameter port, respectively. Utilizing the interpolation equations above [which ones specifically, pls list Eqn (#)], the pressure versus flow relationship for the 0.004 inch EDM and laser drilled ports can be shown relative to the validated ranges, as shown in FIGS. 27 and 28. By reducing the pressure versus flow sensitivity by 2% to account for the 6 degree taper angle of the laser drill process, the upper specification limit USL for the proposed laser port can also be illustrated relative to the validated range. Based on these graphical representations, the laser drilled tip shells with 6 degree taper angle and equivalent inlet port diameters perform with the validated hydraulic resistance envelope for the original straight port EDM catheter.

It is understood that the present invention includes any irrigated ablation tip electrode where any or all of the above ratios are met. That is, an irrigated tip electrode, whether or not it has a two-piece configuration, provides the advantageous features of the present invention where its relevant dimensions and parameters enable the tip electrode to satisfy any or all of the above ratios. The preceding description has been presented with reference to certain exemplary embodiments of the invention. Workers skilled in the art and technology to which this invention pertains will appreciate that alterations and changes to the described structure may be practiced without meaningfully departing from the principal, spirit and scope of this invention. It is understood that the drawings are not necessarily to scale. Accordingly, the foregoing description should not be read as pertaining only to the precise structures described and illustrated in the accompanying drawings. Rather, it should be read as consistent with and as support for the following claims which are to have their fullest and fairest scope.

What is claimed is:

1. An irrigated ablation catheter, comprising:
   an elongated catheter body;
   a deflectable section distal to the catheter body;
   a tip electrode distal to the deflectable section, the tip electrode comprising:
      an outer shell defining a cavity, the shell having a predetermined plurality of fluid ports, each contributing to a total fluid output area of the tip electrode;
      an internal member including a fluid inlet into the tip electrode, the fluid inlet having a fluid input area;
      each fluid port being tapered at an angle greater than 0 to about 10°, and having a fluid port aspect ratio of less than 3.25.

2. The irrigated ablation catheter of claim 1, wherein each fluid port has either an inner inlet diameter between about 0.003 inch and about 0.004 inch, or an outer outlet diameter between about 0.004 inch and 0.005 inch.

3. The irrigated ablation catheter of claim 1, wherein diameters of the fluid ports vary along a length of the tip electrode.

4. The irrigated ablation catheter of claim 3, wherein the diameters of the fluid ports decrease toward a distal end of the tip electrode.

5. The irrigated ablation catheter of claim 1, wherein the fluid port aspect ratio is 1.5 or lower.

6. The irrigated ablation catheter of claim 1, wherein the fluid port aspect ratio is 1.0 or lower.

7. The irrigated ablation catheter of claim 1, wherein the fluid port aspect ratio is 1.0 or lower.

8. An irrigated ablation catheter, comprising:
an elongated catheter body;
a deflectable section distal to the catheter body;
a tip electrode distal to the deflectable section, the tip electrode having a predetermined plurality of fluid ports, each contributing to a total fluid output area of the tip electrode, the tip electrode also having a fluid inlet with a fluid input area;
the tip electrode having a diffusion ratio less than about 2.0;
the total fluid output area of the tip electrode comprising a fluid output area that varies along a length of the tip electrode; and
each fluid port has a tapered configuration.

9. The irrigated ablation catheter of claim 8, wherein the diffusion ratio is 1.8 or less.

10. The irrigated ablation catheter of claim 8, wherein the diffusion ratio is 1.3 or less.

11. The irrigated ablation catheter of claim 8, wherein the tip electrode is configured to deliver a bulk volumetric flow rate of about 8 ml/min to about 15 ml/min.

12. The irrigated ablation catheter of claim 8, wherein the tip electrode is configured to deliver a volumetric flow rate of about 8 ml/min or lower when operated at a wattage below 30.

13. The irrigated ablation catheter of claim 8, wherein the tip electrode is configured to deliver a volumetric flow rate of about 17 ml/min or lower when operated at a wattage of about 30 to about 50.

14. An irrigated ablation catheter, comprising:
an elongated catheter body;
a deflectable section distal to the catheter body;
a tip electrode distal to the deflectable section, the tip electrode comprising:
an outer shell defining a cavity, the shell having a predetermined plurality of fluid ports, each contributing to a total fluid output area of the tip electrode;
an internal member including a fluid inlet into the tip electrode, the fluid inlet having a fluid input area;
the tip electrode having a predetermined diffusion ratio, a fluid port aspect ratio of less than 3.25, and a predetermined inlet aspect ratio;
each fluid port having a tapered configuration; and
at least one of:
the outer shell having a shell thickness of about 0.003 inch to about 0.004 inch; or
each fluid port having an inner inlet diameter of about 0.003 inch to about 0.004 inch; or
each fluid port having an outer outlet diameter of about 0.004 inch to about 0.005 inch.

15. The irrigated ablation catheter of claim 14, wherein the inner diameters and/or outer diameters of the fluid ports vary along a length of the tip electrode.

16. The irrigated ablation catheter of claim 15, wherein the inner and/or outer diameters of the fluid ports decrease toward a distal end of the tip electrode.

17. The irrigated ablation catheter of claim 14, wherein the fluid port aspect ratio is 1.5 or lower.

18. The irrigated ablation catheter of claim 14, wherein the tip electrode is configured to deliver a bulk volumetric flow rate of about 8 ml/min to about 15 ml/min.

19. The irrigated ablation catheter of claim 14, wherein the tip electrode is configured to deliver a volumetric flow rate of about 8 ml/min or lower when operated at a wattage below 30.

20. The irrigated ablation catheter of claim 14, wherein the tip electrode is configured to deliver a volumetric flow rate of about 17 ml/min or lower when operated at a wattage of about 30 to about 50.

* * * * *